United States Patent
Zhang et al.

(10) Patent No.: US 10,815,186 B2
(45) Date of Patent: Oct. 27, 2020

(54) PREPARATION OF VEGETABLE OIL-BASED MONOMERS FOR USE IN THERMOSETTING RESINS

(71) Applicant: Washington State University, Pullman, WA (US)

(72) Inventors: Jinwen Zhang, Pullman, WA (US); Junna Xin, Pullman, WA (US)

(73) Assignee: WASHINGTON STATE UNIVERSITY, Pullman, WA (US)

(*) Notice: Subject to any disclaimer, the term of this patent is extended or adjusted under 35 U.S.C. 154(b) by 0 days.

(21) Appl. No.: 16/669,576

(22) Filed: Oct. 31, 2019

(65) Prior Publication Data
US 2020/0062688 A1 Feb. 27, 2020

Related U.S. Application Data

(62) Division of application No. 15/697,957, filed on Sep. 7, 2017, now Pat. No. 10,513,484.

(60) Provisional application No. 62/384,819, filed on Sep. 8, 2016.

(51) Int. Cl.
*C07C 69/67* (2006.01)
*C07F 7/04* (2006.01)
*C07C 323/52* (2006.01)
*C07D 303/16* (2006.01)
*C07F 7/18* (2006.01)
*C08K 5/10* (2006.01)

(52) U.S. Cl.
CPC ............ *C07C 69/67* (2013.01); *C07C 323/52* (2013.01); *C07D 303/16* (2013.01); *C07F 7/04* (2013.01); *C07F 7/045* (2013.01); *C07F 7/1804* (2013.01); *C08K 5/10* (2013.01)

(58) Field of Classification Search
CPC ....... C07C 69/67; C07C 323/52; C07F 7/045; C07F 7/04; C07F 7/1804; C07D 303/16; C08K 5/10
USPC ........................................................ 549/215
See application file for complete search history.

*Primary Examiner* — Deborah D Carr
(74) *Attorney, Agent, or Firm* — W&C IP

(57) ABSTRACT

The present embodiments herein generally relate to thermoset resins that are derived from vegetable oil based sources, including fibrous plant sources. The utilization of plant based oil as starting materials makes the technology a green alternative to currently available solutions. This, coupled with the novel synthetic methods that are utilized, results in a transformation of the plant based oils into useful, durable, and resilient thermoset resins.

19 Claims, 9 Drawing Sheets

PREPARATION OF VEGETABLE OIL-BASED MONOMERS FOR USE IN THERMOSETTING RESINS

CROSS-REFERENCE TO RELATED APPLICATIONS

This application claims benefit under 35 U.S.C. 119 to U.S. application Ser. No. 62/384,819, entitled "PREPARATION OF VEGETABLE OIL-BASED MONOMERS FOR USE IN THERMOSETTING RESINS", filed on Sep. 8, 2016, and incorporated herein by reference in its entirety.

BACKGROUND

Vegetable oils (VO) and derivatives have been important industrial feedstock chemicals and intermediates. In recent years, there has been a growing interest in development of VO-based alternative thermosetting polymers, such as polyurethanes, unsaturated polyesters, and epoxies. Reactions on the double bonds and ester bonds of the unsaturated fatty chains of VOs may introduce various polymerizable functional groups and, hence, turn VO molecules into bio-based monomers for polymers with less carbon footprint. When the VO-derived monomers are used as co-monomers, the long fatty acid chains of VO provide certain flexibility and/or toughness for some brittle resin systems. However, when utilized alone as base resin monomers, VO-derived monomers tend to give the crosslinked polymer network insufficient modulus and strength. This is mainly due to the VO-based monomers being built on the triglyceride structure in which the polymerizable groups are generally linked by a long flexible fatty chain. This results in polymer materials with poor mechanical properties, which are not appropriate for applications such as composite matrix polymer and protective coatings. There are different ways to improve strength and modulus, including use of rigid co-monomers, curing with rigid hardeners, or increase the crosslink density by introducing more polymerizable groups.

BRIEF SUMMARY

The present embodiments herein generally relate to thermoset resins that are derived from vegetable oil. The vegetable oil may be obtained from fibrous plant sources, such as the hempseed plant. The utilization of plant-based oils as starting materials makes this technology a green alternative to currently available solutions. This, coupled with the novel synthetic methods that are utilized, allow the plant-based oils to be transformed into useful and durable thermoset resins. Thus, the plant-based oils are uniquely transformed to durable and resilient thermoset resins.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
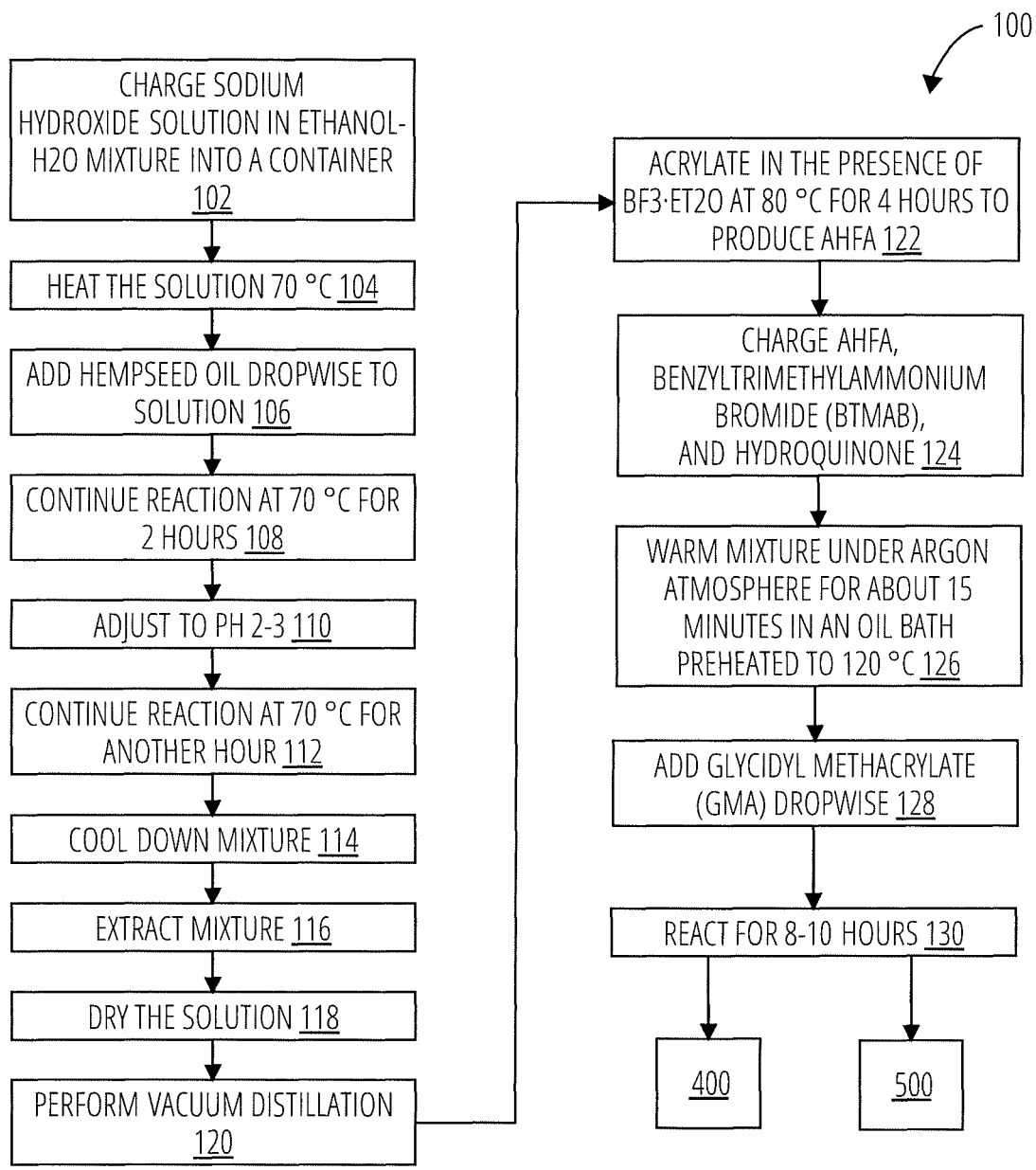
FIG. 1 illustrates an embodiment of a monomer production process 100.

Disclosed herein are biobased monomer compounds derived from fatty acids (FAs) that are the hydrolysis products of VOs. VO-based polymer materials are mostly based on the monomers obtained by derivatization of the carbon-carbon double bonds in the chains of the unsaturated fatty acids of the oil (Scheme 1a). Therefore, when the monomer is built on the triglyceride structure of the oil, the properties of the resulting thermoset is determined by the distance between the two polymerizable groups from one fatty acid to another fatty acid on the same oil structure. This distance is the same as that from a double bond of one unsaturated fatty acid to the double bond of another unsaturated fatty acid and is at least 21 single chemical bonds, making the cured thermosets soft. When the monomer is directly built on the structure of an unsaturated FA derived from hydrolysis of oil, one polymerizable group is introduced through the carboxyl end group of the FA, in addition to the ones derived from the double bonds, as shown in Scheme 1b. In this way, the distance between two polymerizable groups is reduced (it is 16 in Scheme 1b). As a result, thermosetting polymers based on the FA-derived monomers tend to give higher crosslink density, resulting in improved strength and modulus. The FAs that may be utilized may be obtained from a variety of resources, including hempseed oil, cottonseed oil, soybean oil, castor oil, tung oil, and linseed oil. Three types of FA-derived monomers are presented by way of example: acrylate monomers, thiol-containing monomers, and silane-containing monomers. These monomers may be polymerized or co-polymerized via either thermal initiation or photo initiation to form crosslinked network structures.

Scheme 1. Illustration of different carbon chain lengths between epoxy groups for monomer based on triglyceride structure of oil and monomer based on fatty acid.

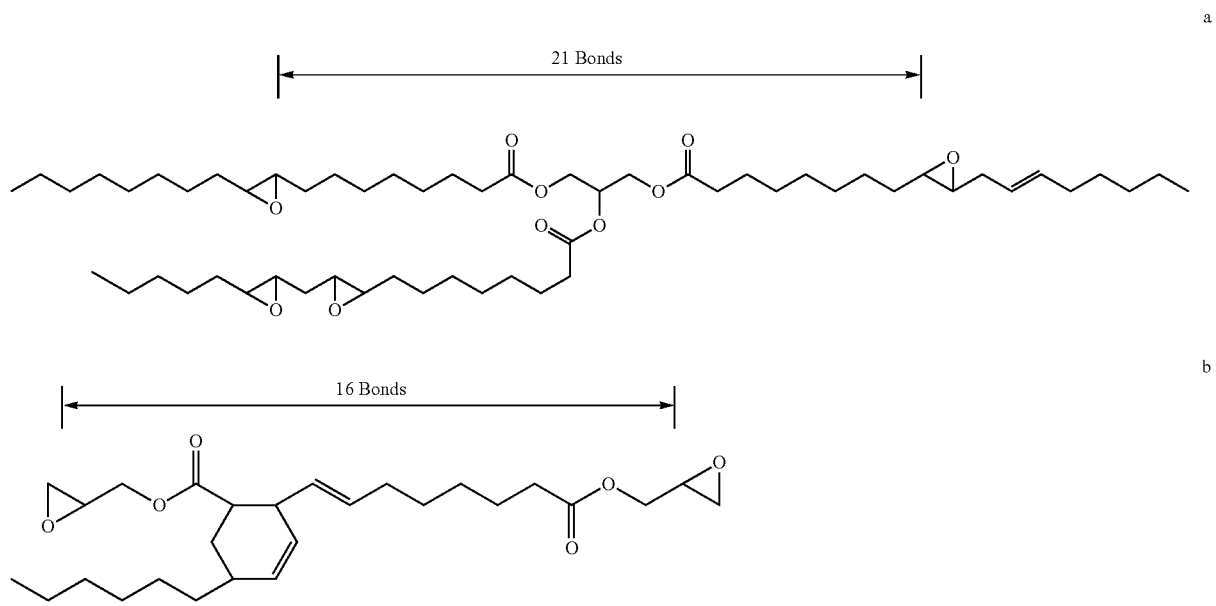

Hydrolysis of Hempseed Oil

In one embodiment, a sodium hydroxide (16 g) solution in 140 mL ethanol-$H_2O$ (1:1, V/V) is charged into a 1-L three-necked round-bottom flask equipped with reflux condenser, magnetic stirrer, and thermometer. After the solution is heated to 70° C., hempseed oil (100 g) is dropwise added to the reaction system using a dropping funnel. The reaction is continued at 70° C. for 2 hours. After that, the reaction mixture is adjusted to pH 2-3 using 1 M hydrochloric acid, and then the reaction is continued at 70° C. for another hour. After the reaction is cooled down, the mixture is extracted with ethyl ether and is washed with de-ionized (DI) water three times. The ethyl ether solution is dried over magnesium sulfate. Finally, the ethyl ether is removed by vacuum distillation, resulting in a viscous mixture of hydrolyzed hempseed oil fatty acids (HFA, yield 90%). The composition of fatty acids in hydrolyzed hempseed oil is determined by Gas Chromatography—Flame Ionization Detector (GC-FID) using a standard fatty acid methyl esters (FAME) procedure.

Acrylation of Hydrolyzed Hempseed Oil Fatty Acid (HFA)

The HFA is directly acrylated in the presence of $BF_3.Et_2O$, as shown in Scheme 2. Representative reaction conditions are as follows: the mixture of HFA, acrylic acid (AA) and $BF_3.Et_2O$ in the molar ratios of 1:27.4:1.37 are reacted under stirring at 80° C. for 4 hours. Depending on the size of reaction, two different work-up procedures may be employed. For the small size reactions, the excess AA and catalyst are removed by $NaHCO_3$ aq. washing directly. For the large size reactions, the excess AA and catalyst are recovered by distillation at 35-45° C. under reduced pressure, and the recovered AA and catalyst are reused. The yellow liquid acrylate hempseed oil fatty acid (AHFA) is obtained (yield 90%).

Methacrylation of AHFA

A 100-mL round-bottom flask equipped with a magnetic stirrer is charged with 0.10 mol AHFA, 0.002 mol (2 mol % on fatty acid) of benzyl trimethyl ammonium bromide (BTMAB), and 1 wt % hydroquinone. The mixture is allowed to warm under argon atmosphere for about 15 minutes in an oil bath preheated to 120° C. Glycidyl methacrylate (GMA, 0.11 mol) is subsequently added dropwise using a dropping funnel. The reaction progress is monitored over 6 hours by thin layer chromatograph (TLC) using methylene chloride and ethyl acetate (7:3). Due to the competing side reactions, further addition of up to 0.1 molar equivalent of GMA and additional reaction time may be utilized to react all of the AHFA. Two major oxirane ring-opening products are observed as the reaction proceeded to completion within a total of 8-10 hours. To produce a purified sample for characterizations, the dark-colored reaction mixture is allowed to cool to room temperature and then passed through a short silica (200 mesh) column using 20% ethyl acetate in methylene chloride to remove the catalyst and dark brown particulates. A yellowish brown liquid AHFA-GMA (mixture of 1a & 1b, yield 75-86%) is obtained.

Scheme 2. Hempseed oil fatty acid-derived acrylate.

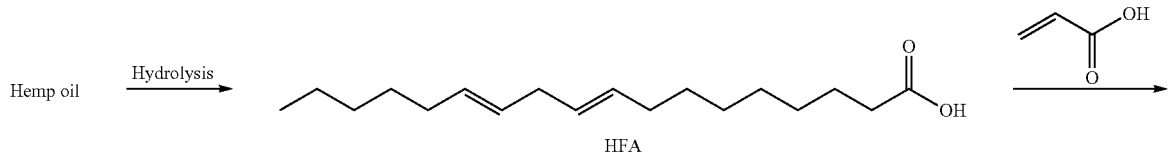

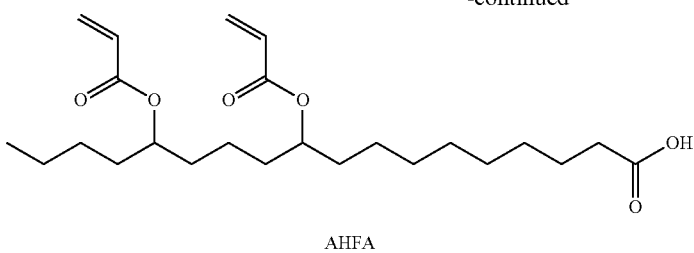

AHFA

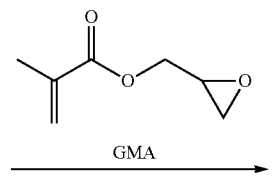

GMA

-continued

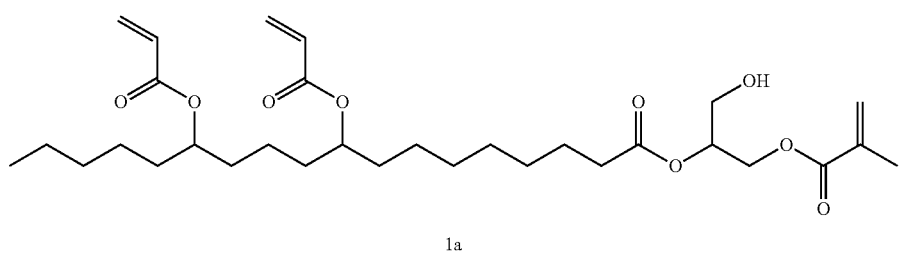

1a

+

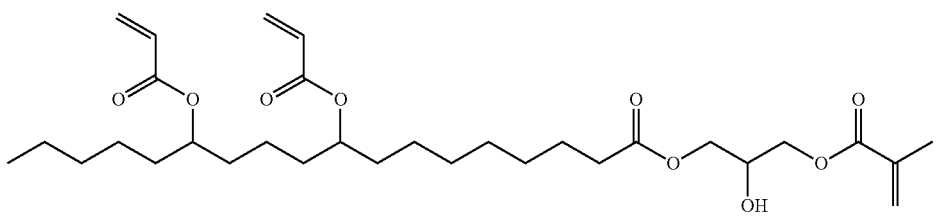

1b

AHFA-GMA

Synthesis of Castor Oil Fatty Acid Methacrylates (2a & 2b)

In another embodiment, the synthesis of the compound depicted in Scheme 3 is achieved in a two-step process. A 100-mL round-bottom flask equipped with a magnetic stirrer is charged with 29.85 g (0.10 mol) ricinoleic acid (RA, from castor oil), 0.46 g (0.002 mol, 2 mol % on the basis of fatty acid) BTMAB, and 0.3 g (1 wt %) of hydroquinone. The mixture is allowed to warm under argon atmosphere for about 15 minutes in an oil bath preheated to 120° C. Glycidyl methacrylate (GMA, 15.63 g (1.1 equivalent)) is subsequently added dropwise using a dropping funnel. The reaction progress is monitored over 6 hours by TLC. Due to the competing side reactions, further addition of up to 0.1 equivalent of GMA and additional reaction time may be utilized to ensure all of the RA reacted. Two major oxirane ring-opening products are produced as the reaction proceeded to completion within a total of 8-10 hours. To prepare the purified sample for characterizations, the dark-colored reaction mixture is allowed to cool to room temperature and passed through a short silica (200 mesh) column using 20% ethyl acetate in methylene chloride to remove the catalyst and dark brown particulates. A yellowish brown liquid (RA-GMA) is obtained (yield 75-87%).

Before the dropwise addition (46.25 g, 0.3 mol; 3 equivalent to RA) of methacrylic anhydride (MAA) to the product mixture from above, a catalytic amount (0.12 g, 1 mol %) of 4-(dimethylamino)pyridine (DMAP), 30.35 g triethylamine (TEA) (3 molar excess), and 1 wt % hydroquinone are added. The reaction is allowed to proceed optimally at 70° C. and monitored by TLC for 4-6 hours under argon atmosphere. TLC determined the presence of one major product in addition to some minor impurities that account for unreacted excess methacrylic anhydride, residual traces of GMA and dimethacrylates. The reddish brown reaction mixture is dissolved in ~300 mL of methylene chloride and washed with 500 mL (6×~80 mL) each of distilled $H_2O$, 10% (v/v) dilute hydrochloric acid, saturated sodium bicarbonate ($NaHCO_3$) solution and saturated brine. The organic phase is dried over anhydrous magnesium sulfate ($MgSO_4$) and concentrated under reduced pressure at no more than 60° C., yielding ~40 g yellowish-dark brown liquid product MARA-GMA (mixture of 2a & 2b). To prevent premature gelation, the product is stored in a closed container, away from direct sunlight, UV, and heat sources.

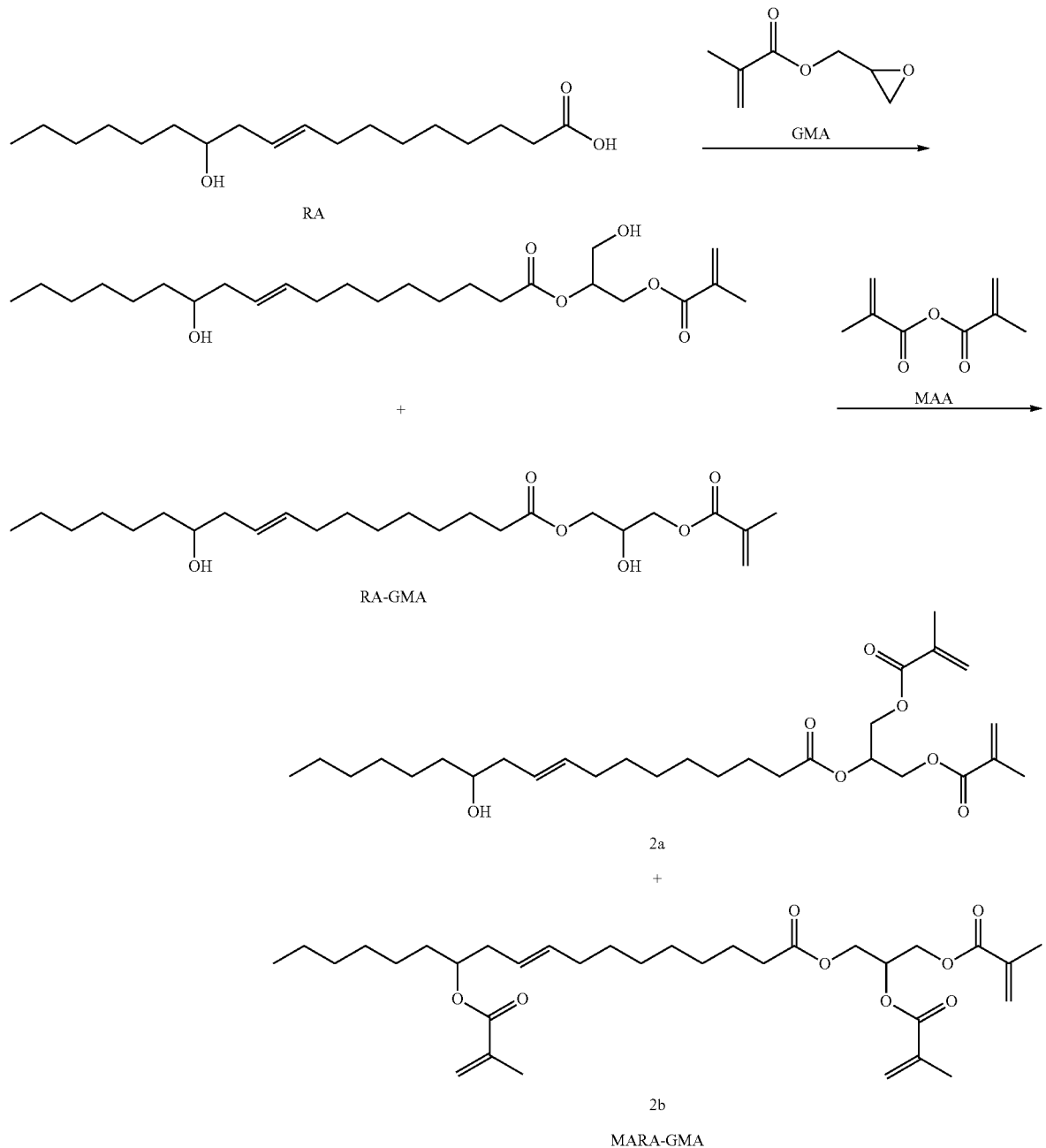

Scheme 3. Synthesis of castor oil fatty acid methacrylates.

Another embodiment is depicted in Scheme 4, which illustrates the synthesis of the acrylate compounds 3 & 4 in a three-step process. After 28 g HFA and 21.2 g sodium carbonate are mixed well in 20 mL methylene chloride (CH$_2$Cl$_2$), 73.6 g meta-chloroperoxybenzoic acid (m-CPBA, 75 wt %) dissolved in CH$_2$Cl$_2$ at 0.1 g/ml concentration is added dropwise at a reaction temperature below 15° C., and then the reaction is reacted for 4 hours to complete the epoxidation. The reaction mixture is washed with 10 wt % sodium sulfite and then by 10 wt % aqueous sodium bicarbonate. CH$_2$Cl$_2$ is removed by in vacuum rotary evaporation and 30 g product epoxidized hempseed oil fatty acid (EHFA, 96% yield) is obtained.

31.2 g EHFA, 0.46 g, BTMAB, and 0.3 g (1 wt %) of hydroquinone is mixed well in flask. After the mixture is protected under argon atmosphere and placed in an oil bath of 120° C. for about 15 minutes, glycidyl methacrylate (GMA, 15.63 g (1.1 equivalent)) is added dropwise. The reaction progress is monitored over 6 hours by TLC. Next, the reaction mixture is purified by silica gel column to remove the impurity by ethyl acetate and methylene chloride, then product EHFA-GMA is obtained with the yield 87%.

45.4 g EHFA-GMA, 1.15 g BTMAB, and 0.9 g (2 wt %) of hydroquinone is mixed and allowed to warm under argon atmosphere for about 15 minutes in an oil bath preheated to 100° C. The mixture of acrylic acid/acrylic anhydride (R=H) or methyl acrylic acid/methacrylic anhydride (R=CH$_3$) (acid/anhydride=0.15 mol/0.3 mol) is added dropwise into the reaction mixture. The reaction progress is monitored over 6 hours by TLC. Subsequently, the reaction mixture is purified by silica gel column to remove the impurity by ethyl acetate and methylene chloride, then products 3 and 4 are obtained with the yield 65% and 72%, respectively.

AHFA-GMA-A-Silane (Scheme 5-I), RA-GMA-A-Silane (Scheme 5-II), or EHFA-AA/MA-GMA-A-Silane (Scheme 5-III), respectively. A methacrylate functional group may also be utilized to produce AHFA-GMA-MA-Silane, RA-GMA-MA-Silane, or EHFA-AA/MA-GMA-MA-Silane when using methacrylate silane as the silane agent.

The fatty acid derivatives with multi-acrylic silane groups are prepared by the following general procedure. The reactions are carried out in a flask equipped with a stirrer,

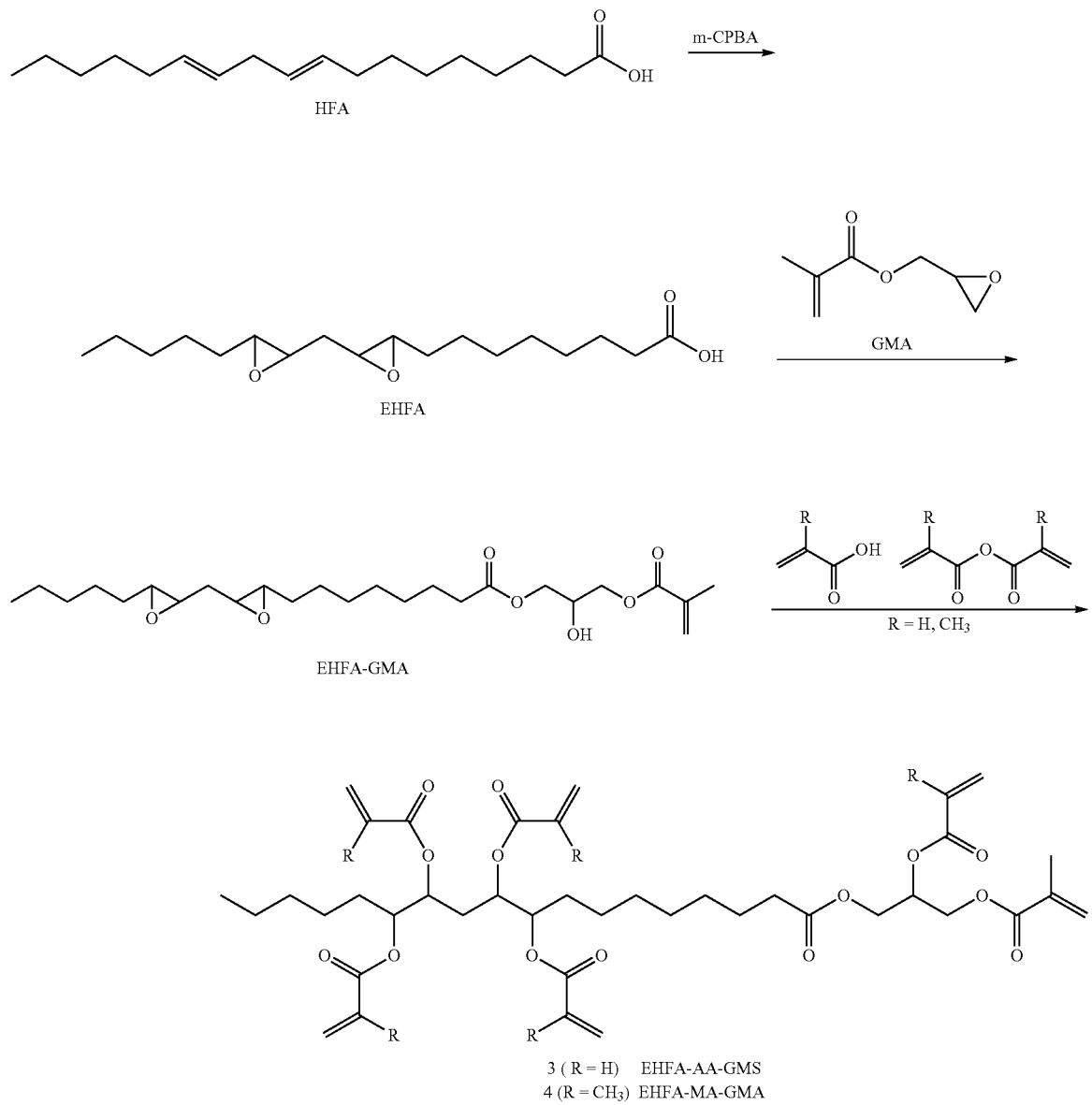

Scheme 4. Synthesis of fatty acid derivatives with multi-acrylic groups.

Silane Modified (Dual Curing, Moisture Curable)

Another embodiment is depicted in Scheme 5, which depicts silane-modified acrylated or methacrylated FA through residual hydroxyls. As depicted, the result in Scheme 2 (referred to as (1)), RA-GMA (an intermediary in Scheme 3, prior to reacting with MAA), and 3 & 4 (EHFA-AA/MA-GMA, a derivative from the intermediary in Scheme 4) is reacted with an acrylate silane group to form dropping funnel, thermometer, and reflux condenser capped with a drying tube. Silane agent is mixed with AHFA-GMA, RA-GMA, or EHFA-AA/MA-GMA at a molar ratio of 1:1 to 1:4 (based on the hydroxyl groups containing in the reagents), and the mixture is stirred for 2-3 h at 90-100° C. Liberated methanol is distilled off under reduced pressure (on a rotary evaporator), giving the products with the yield of 67-75%.

Scheme 5. Synthesis of fatty acid derivatives with multi-acrylic silane groups.
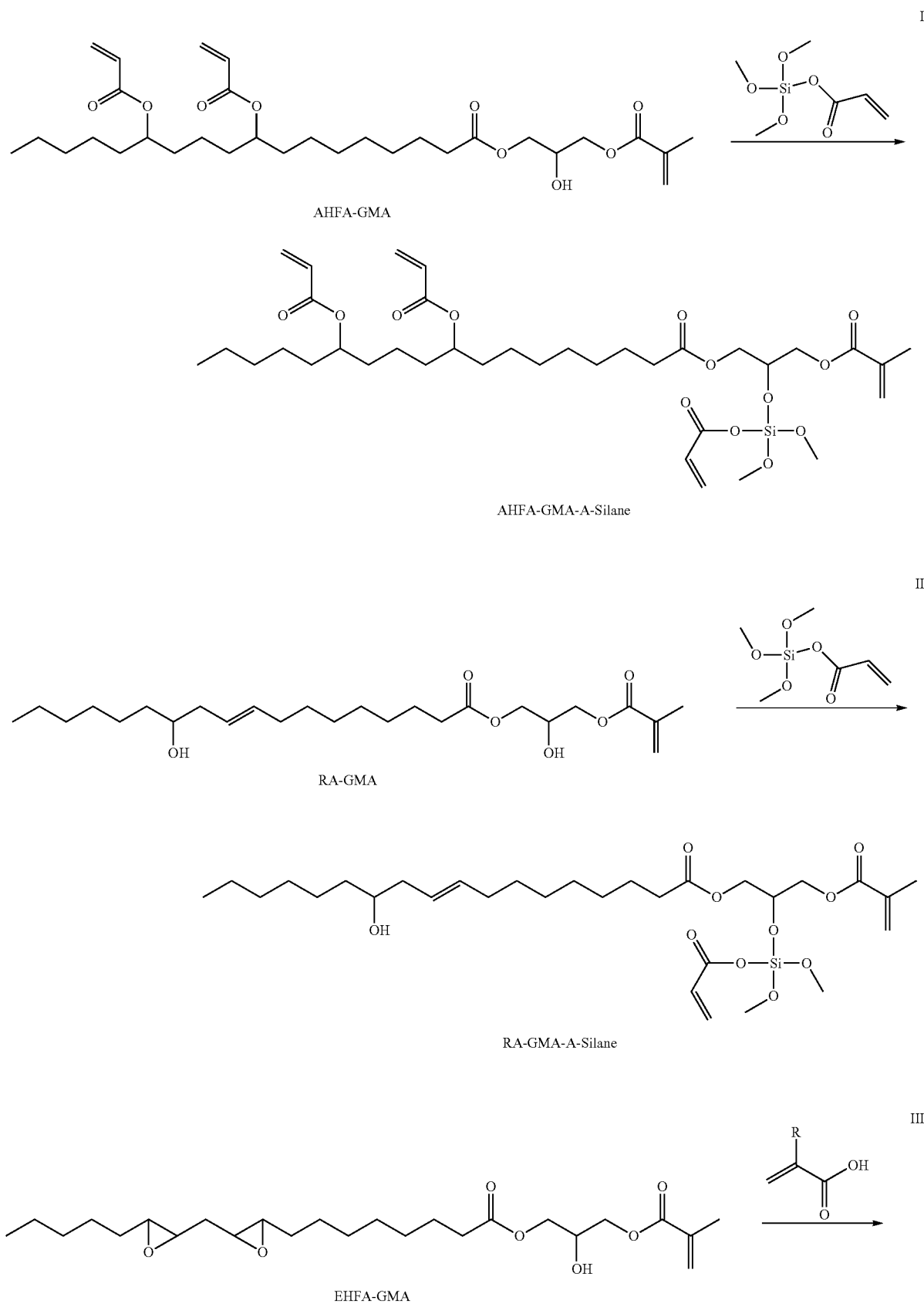

-continued

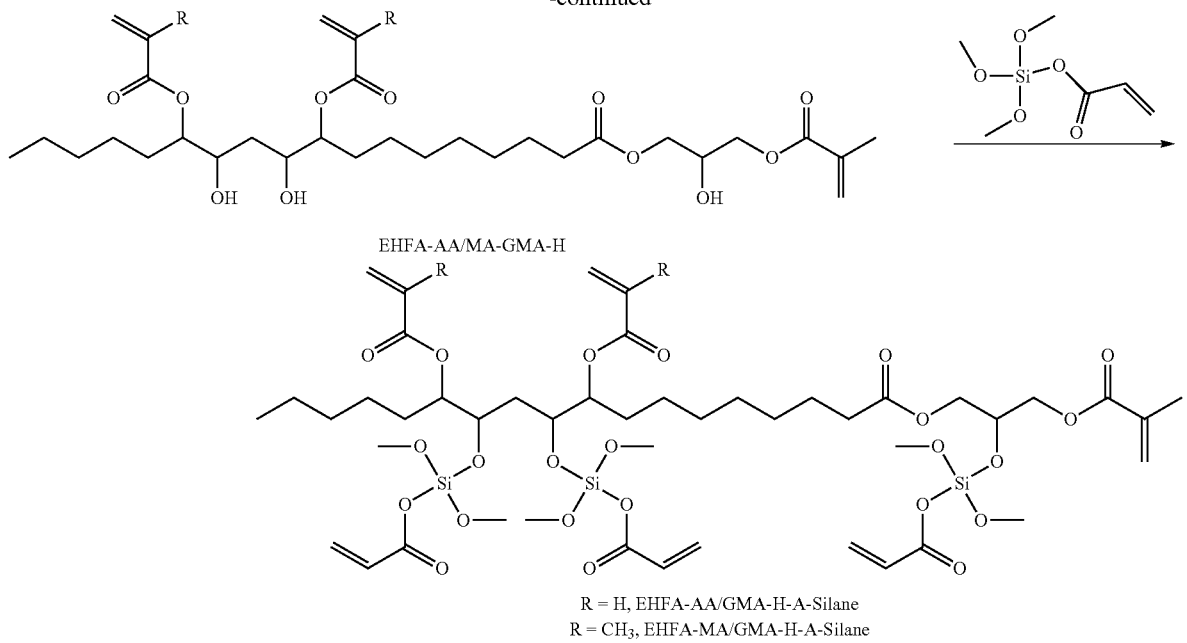

EHFA-AA/MA-GMA-H

R = H, EHFA-AA/GMA-H-A-Silane
R = CH₃, EHFA-MA/GMA-H-A-Silane

Another embodiment is depicted in Scheme 6, which depicts silane-modified (meth)acrylate FA through residual hydroxyls. This process is similar to Scheme 5; however, vinyl functional silane replaces acrylate/methacrylate-silane to produce AHFA-GMA-V-Silane, RA-GMA-V-Silane, and EHFA-AA/MA-H-V-Silane.

The fatty acid derivatives with multi-vinyl silane groups are prepared by the following general procedure. The reactions are carried out in a flask equipped with a stirrer, dropping funnel, thermometer, and reflux condenser capped with a drying tube. Silane agent is mixed with AHFA-GMA, RA-GMA or EFA-AA/MA-GMA-H at a molar ratio of 1:1 to 1:4 (based on the hydroxyl groups containing in the reagents), and the mixture is stirred for 2-3 h at 90-100° C. Liberated methanol is distilled off under reduced pressure (on a rotary evaporator), giving the products with the yield of 77-85%.

Scheme 6. Synthesis of fatty acid derivatives with multi-vinyl silane groups.

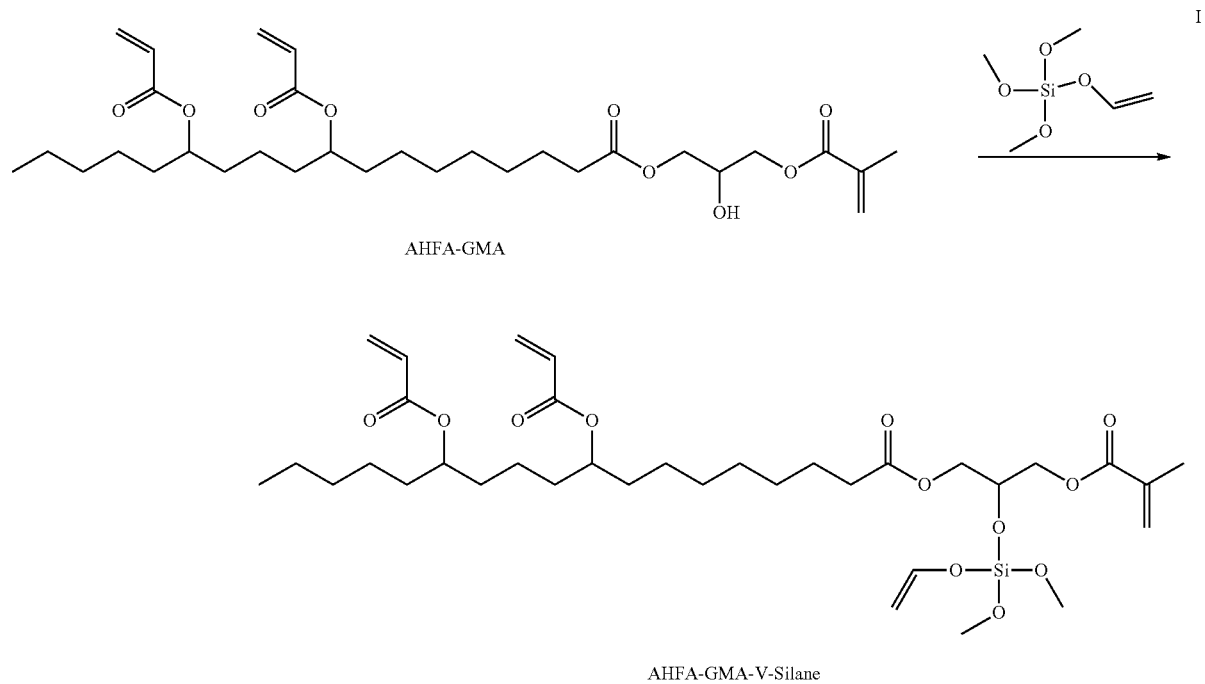

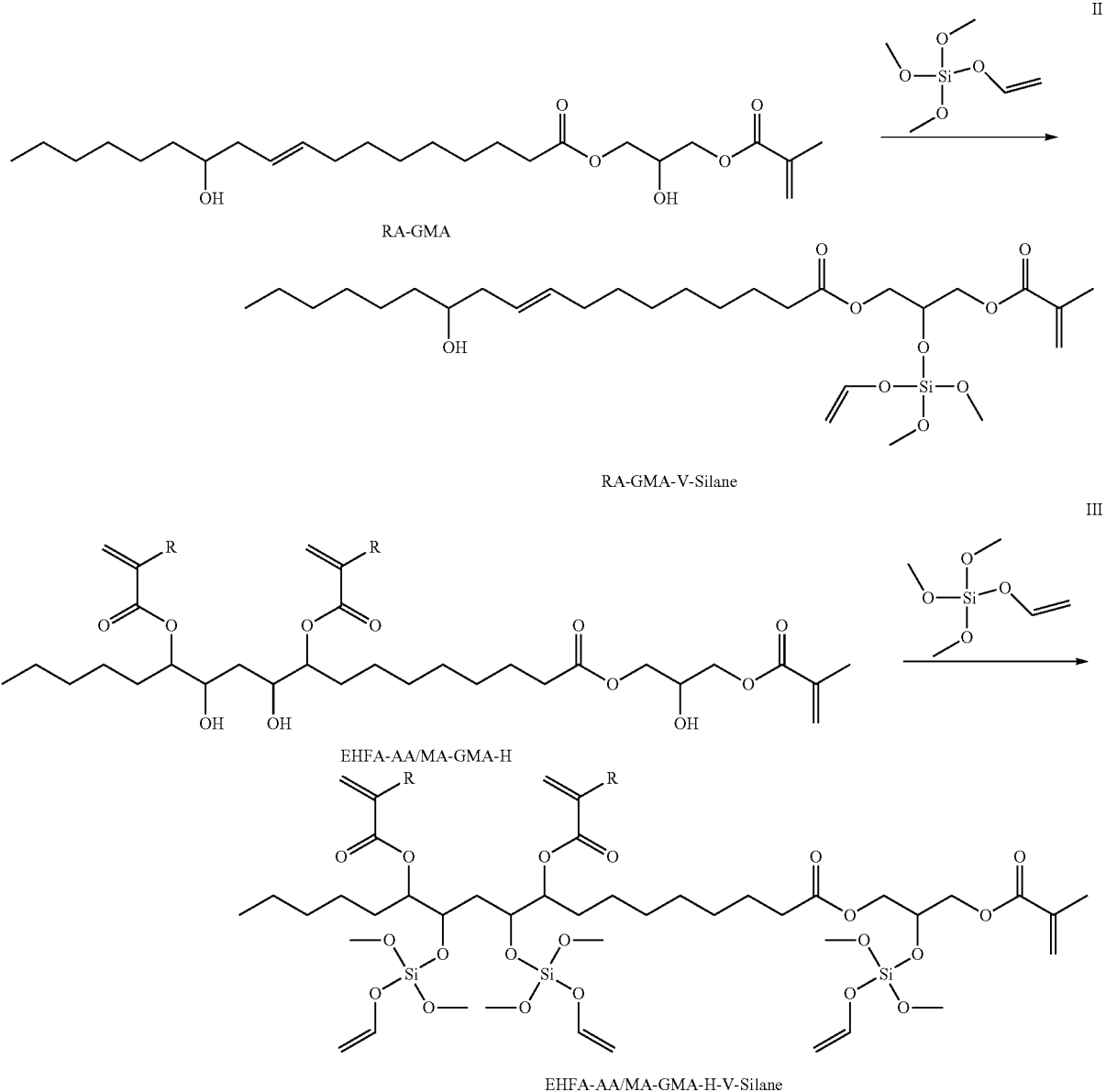

Epoxy Type

Yet another embodiment is depicted in Scheme 7, which depicts fatty acid-derived epoxy (dimer acid-derived, and fatty acid-derived diacid and triacid). In one embodiment, the dimer acid (DA) is reacted with epichlorohydrin (ECH) to form DA-diepoxy (as shown in Scheme 7-I). In another embodiment, the FA is first reacted with either acrylic acid or fumaric acid to produce fatty acid-derived diacid (FA-diacid) and fatty acid-derived triacid (FA-triacid), which are then reacted with ECH to produce a FA-diepoxy or FA-triepoxy (as shown in Scheme 7-II & 7-III).

The preparation of DA-diepoxy follows a general procedure stated here. To a 50 mL flask equipped with reflux condenser, magnetic stirrer, and thermometer are charged 3.74 g DA, 18.5 g epichlorohydrin, and 0.023 g benzyltriethyl ammonium chloride. The reaction temperature is raised to 117° C. and the reaction continued at that temperature for 2 h. After the mixture is cooled to 60° C., 0.8 g sodium hydroxide and 1.12 g calcium oxide is charged. The mixture is stirred at 60° C. for 3 h and then filtered by diatomaceous earth (e.g., Celite®) and filter paper. The solid is discarded. After the excess epichlorohydrin is distilled under vacuum at 100° C. from the filtrate, a light yellowish liquid product is obtained with a yield of 85%-90%. Since the dimer fatty acid is a mixture of various isomers with similar structures, DA-diepoxy is not further purified and utilized as prepared.

The preparations of FA-triacid follow a general procedure stated here. 129 g crude adduct of fumaric acid and conjugated FA is dissolved in 500 mL acetone and neutralized by 50% NaOH solution drop by drop until the pH value reaches 7. After the acetone is removed, the precipitated tricarboxylic acid is extracted with ethyl acetate. The organic layer is neutralized using HCl and dried by NaSO$_4$ for 12 h and then the ethyl acetate is removed using a vacuum rotary evaporator to obtain a white solid FA-triacid (yield: 99%).

3.5 g FA-triacid, 18.5 g epichlorohydrin, and 0.061 g benzyltriethyl ammonium chloride are added to a 50-mL flask. The reaction temperature is raised to 117° C. and the reaction continued for 2 h. After the mixture is cooled to 60° C., 1.2 g sodium hydroxide and 1.68 g calcium oxide are charged. The mixture is stirred at 60° C. for 3 h and then filtered with powder Celite. After the excess epichlorohydrin is distilled under vacuum at 100° C. from the filtrate, a yellowish viscous product (4.56 g) is obtained. The product is purified using a silica gel column (ethyl acetate:hexane=1:4 v/v) to receive 4.00 g of FA-triepoxy (yield: 88%) with an epoxide equivalent weight 193 g/mol (theory: 187 g/mol).

Fatty acids (100 g) and hydroquinone (0.25 g) are charged into a flask. The temperature is raised to 160° C., and acrylic acid (24.7 g) is added slowly. The reaction is continued for 5 h at 160° C. after all the acrylic acid is added. The excess acrylic acid is first removed using a rotary evaporator under vacuum, and then the crude product is distilled under a 5 mmHg vacuum. The fraction between 210 to 240° C. is collected, receiving 103 g of yellowish liquid FA-diacid (yield: 97%).

The preparations of FA-diepxoy and FA-triepoxy follow a general procedure describe here. The synthesis of FA-diepoxy is similar to that of FA-triepoxy. The product is purified using a silica gel column (ethyl acetate:hexane=1:4 v/v), and the yield of pure FA-diepoxy is 85%. The EEW of FA-diepoxy is 235 g/mol (theory: 231 g/mol).

Scheme 7. Synthesis of FA derived epoxy monomer.

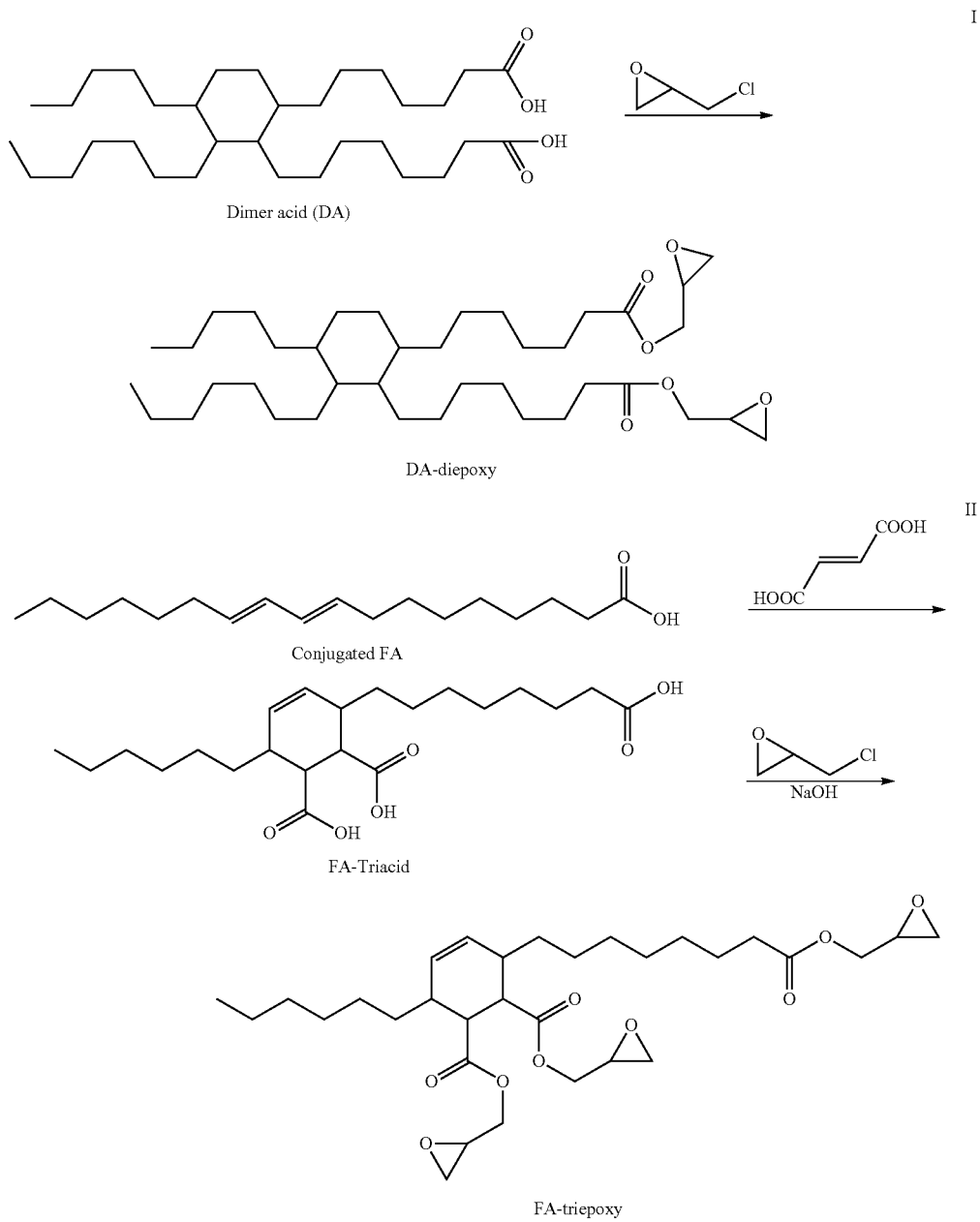

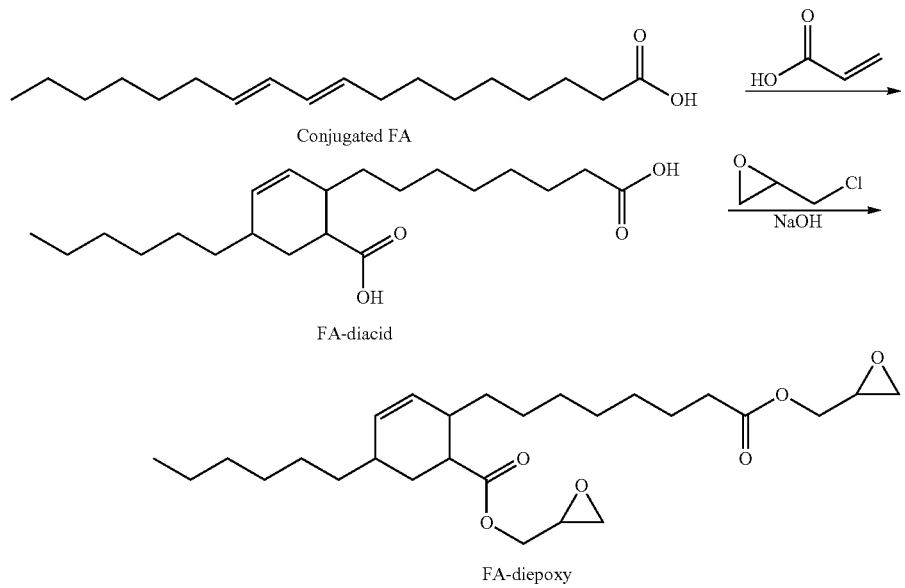

Yet another embodiment is depicted in Scheme 8, which depicts silane modified epoxy (dual curing, moisture curable). The DA is reacted with the silane-modified epoxy to produce the DA-silane-epoxy.

The silicon epoxy compound 59 g, DA 50 g, toluene 75 g, trifluoroacetic acid 0.37 g are charged into a 250 mL flask equipped with a nitrogen gas, thermometer and Dimroth condenser. The reaction is first conducted at 120° C. under stirring for 1 hour; subsequently, the temperature is gradually raised to 140° C. by distillation removing the generated methanol with toluene. The reaction is continued for 3 hours at 140° C., and then the remaining toluene is distilled off under reduced pressure. A transparent liquid product of 88 g (yield 78%, DA-diepoxy-Silane) is obtained.

Scheme 8. Synthesis of DA-diepoxy-Silane.

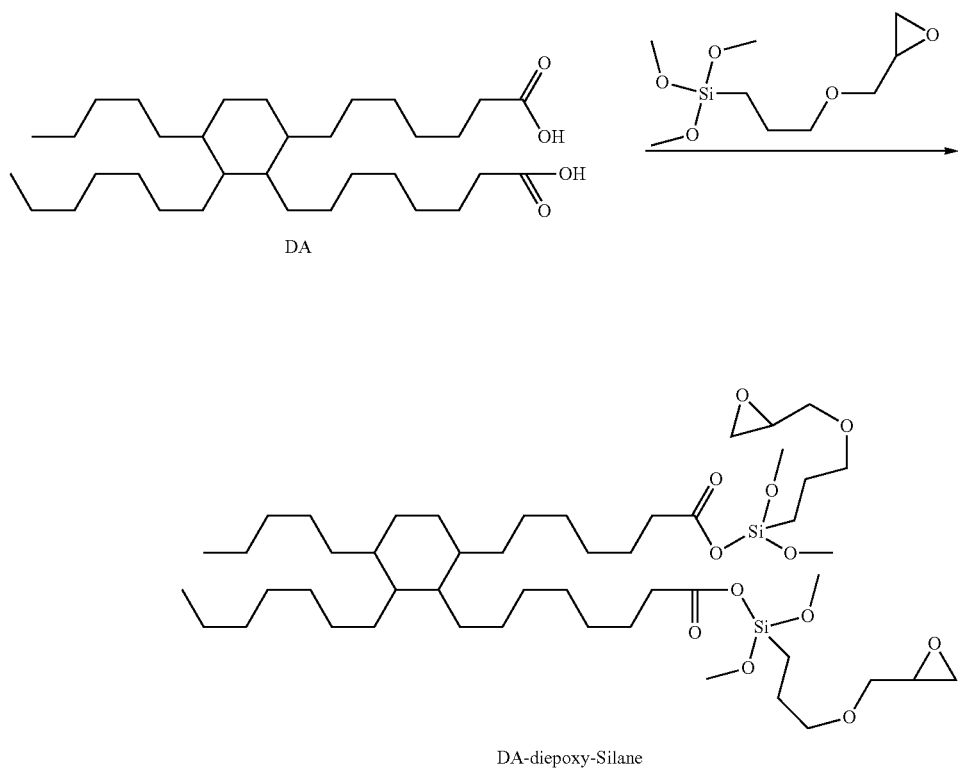

Thio Compound Curing Agents

In another embodiment, depicted in Scheme 9, fatty acid-derived thio-compounds are utilized as curing agents (e.g., mercaptopropionic acid). The EHFA (such as a HFA reacted with m-CPBA above) undergoes methanolysis prior to being reacted with 2-chloroethanol. The intermediary is then reacted with mercaptopropionic acid to produce the FA-derived thio compound.

MEHFA is synthesized by oxirane ring opening reaction via refluxing EHFA (100 g) with excess methanol (136 g) in the presence of tetra-fluoroboric acid catalyst. The molar ratio of epoxy groups to methanol is 1:11. The concentration of the catalyst is 1% of the total weight of the EHFA and methanol. HFA, methanol and catalyst (amount of each reagent as described above) are added into a flask, then stirred and reflux for 1 h. After being cooled to room temperature, ammonia (30% in water) is added to neutralize the reaction mixture pH to 7. The solvent is removed on a rotary evaporator under a low vacuum at 60-95° C. The product of MEHFA is obtained with a yield of ~98%.

Hydroquinone (3.0 g) and NaOH (8 g) are added to the mixture of 75.2 g MEHFA and 48.3 g 2-chloroethanol at room temperature and under stirring. After the mixture is refluxed for 4 h, it is cooled down to room temperature and filtered to remove the precipitate. The filtrate is added to a large amount of water, and the product MEHFA-triol is precipitated (yield ~83%).

The mixture of MEHFA-triol (42.0 g), 3-Mercaptopropionic acid (40.0 g), and 1 wt % p-toluenesulfonic acid (p-TSA) solution (200 mL) in toluene in a 500 mL flask is refluxed for 4 h. After being cooled down, the mixture is extracted by ethyl estate, and the organic layer is washed by water. After the solvent is removed by rotatory evaporator, the resulting solid is dried by MgSO4 to give the product 5 (yield: 73-89%).

Scheme 9. Synthesis of FA derived silicon-containing thiol compound.

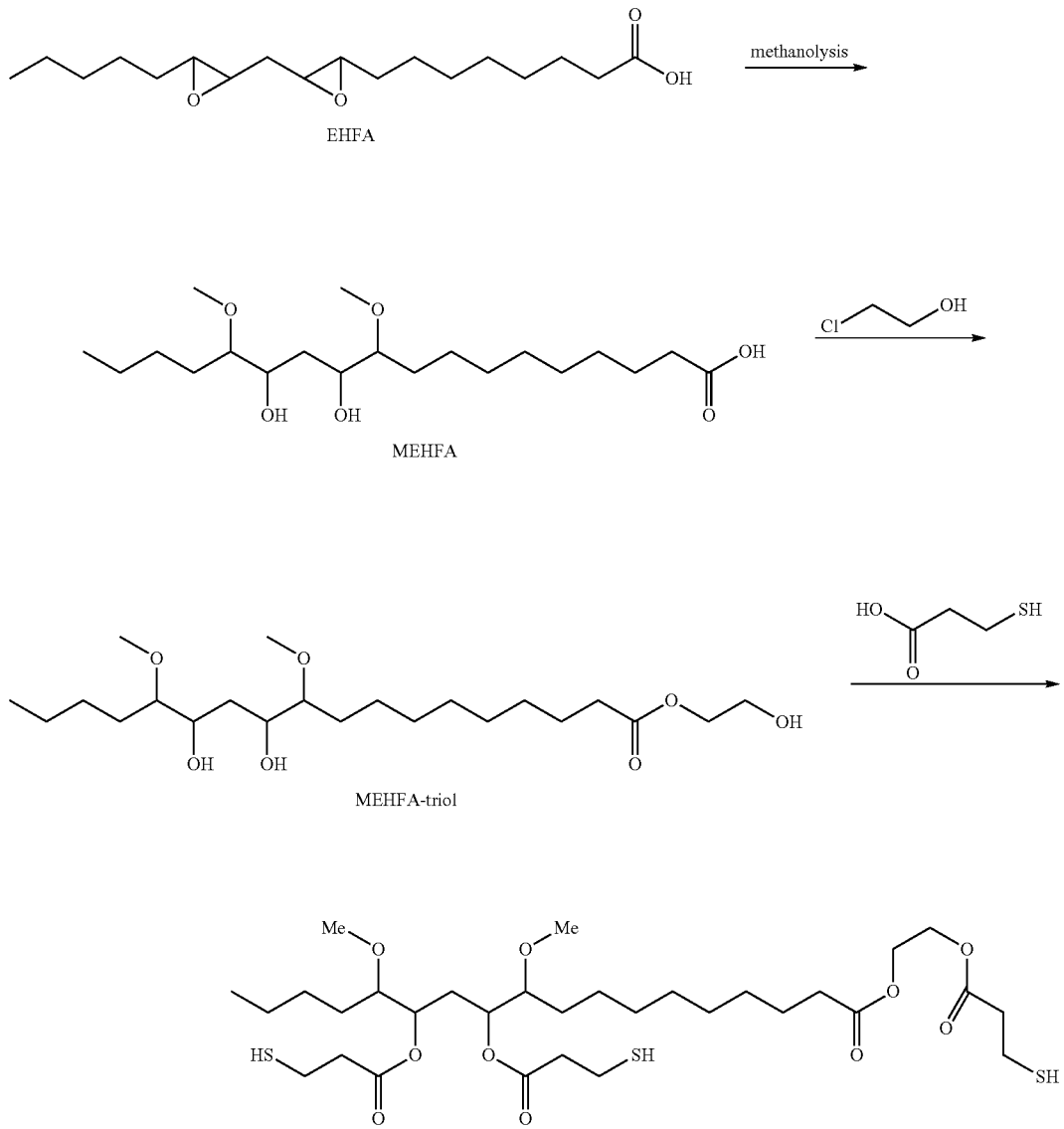

Another embodiment is depicted in Scheme 10, which depicts the utilization of sulfur (mercapto) functional silane. The intermediary depicted in Scheme 9 is reacted with mercapto-functional silane instead of mercaptopropionic acid to produce the FA-mercapto-functional silane. The reaction procedure is similar to that in Scheme 5. MEHFA-triol-silane is obtained with a yield of ~79-85%.

commercial bisphenol A epoxy resin D.E.R.™ 332 (DER332). They also exhibited higher reactivity than DER332 during curing. After curing with the same curing agent, nadic methyl anhydride, the resulting resins exhibited $T_g$s as follows: DER332 (168° C.)>FA-triepoxy (131° C.)>FA-diepoxy (80° C.)>epoxidized soybean oil (ESO, 37° C.) as shown in Table 2. The difference in thermal and Scheme 10. Synthesis of FA derived silicon-containing thiol compound.

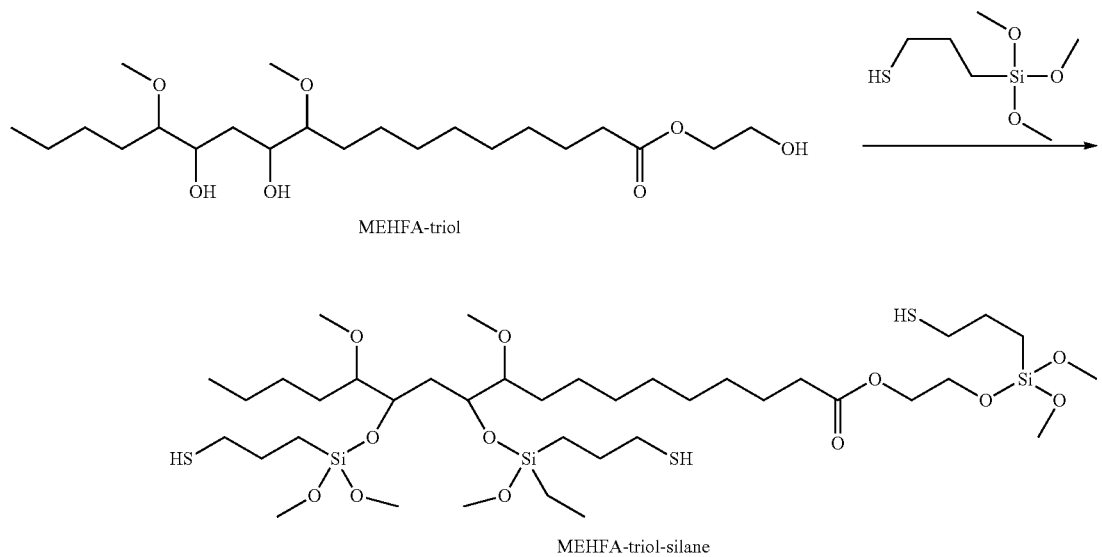

MEHFA-triol

MEHFA-triol-silane

Unless otherwise state above, tolerances for mass, volume, temperature, pH, molarity, and time is ±10.

mechanical properties for the FA-derived resins is likely attributed to the difference in their crosslink densities. That

TABLE 1

Flexural properties and $T_g$s of cured epoxies with different DA-diepoxy/Rosin based diepoxy (DGEAPA) weight ratios

| Samples | DGEAPA/DA-diepoxy (% DA-diepoxy in epoxy mixture) | Flexural strength (MPa) | Elastic modulus (GPa) | Flexural strain % | $T_g$ (° C.) |
|---|---|---|---|---|---|
| a | 5:0 (0) | 108.5 ± 9.2 | 3.11 ± 0.15 | 3.7* ± 0.3 | 185 |
| b | 5:1 (16.7%) | 119.5 ± 8.8 | 2.91 ± 0.07 | 4.5* ± 0.3 | 163 |
| c | 5:3 (37.5%) | 120.1 ± 6.1 | 2.63 ± 0.03 | 6.5** ± 0.8 | 132 |
| d | 5:5 (50%) | 106.6 ± 4.0 | 2.39 ± 0.05 | 6.6** ± 0.2 | 114 |
| e | 1:5 (83.3%) | 50.7 ± 4.6 | 1.31 ± 0.08 | 5.6** ± 0.4 | 65 |
| f | 0:5 (100%) | 4.4 ± 0.2 | 0.12 ± 0.02 | 8.0** ± 1.0 | 43 |

* at break, ** at yield. From K. Huang, J. Zhang, M. Li, J. Xia, Y. Zhou, *Industrial Crops and Products* 2013, 49, 497-506.

As shown in Table 1, because of its long fatty chain, the cured DA-diepoxy resin alone exhibited a low glass transition temperature, $T_g$ (43° C.), flexural strength (4.4 MPa) and modulus (0.12 GPa) (Table 1). In contrast, the cured rigid DGEAPA displayed high $T_g$ (185° C.), flexural strength (108.5 MPa) and modulus (3.11 GPa). Addition of dimer acid-derived epoxy may flexibilize and toughen the rosin-derived epoxy resin. From the application perspective, the mixed epoxies containing 20-40 wt % of DA-diepoxy exhibit overall high performance. The results suggest that the rigid DGEAPA and the flexible DA-diepoxy are complementary in many physical properties and the mixture of the two in appropriate ratios may result in well-balanced properties.

Both FA-diepoxy and FA-triepoxy are liquid at room temperature and have lower viscosity than that of the also explains why the $T_g$ of the cured FA-diepoxy (80° C.) was lower than that of the cured FA-triepoxy (131° C.) but higher than that of ESO (37° C.). Because DER332 is a more rigid molecule than FA-triepoxy, it exhibited the highest $T_g$ among all the cure epoxies presented. Results from bending tests indicate that the cured FA-triepoxy and DER332 had similar flexural strengths, but the latter had higher elastic modulus. In contrast, the cured FA-diepoxy exhibited a lower flexural strength but a comparable modulus to that of the cured FA-triepoxy. TGA results indicate that the FA-derived epoxies exhibited thermal stability similar to that of DER332. The results also demonstrate that FA-diepoxy and FA-triepoxy are superior to ESO for epoxy applications.

TABLE 2

Flexural, impact properties and crosslink densities of NMA (nadic methyl anhydride) cured FA-diepoxy, FA-triepoxy and D.E.R. 332 (Bisphenol A type epoxy)

| Samples | Flexural properties | | | Impact strength | $T_g$ (° C.) |
| --- | --- | --- | --- | --- | --- |
| | stress (MPa) | modulus (MPa) | strain (%) | (KJ/m$^2$) | |
| FA-diepoxy | 88.6 ± 2.1$^a$ | 2211.4 ± 56.4$^a$ | 8.1 ± 0.02$^a$ | 9.3 ± 1.3 | 80 |
| FA-triepoxy | 121.4 ± 2.0$^b$ | 2621.3 ± 65.4$^b$ | 8.7 ± 0.2$^b$ | 7.9 ± 1.4 | 131 |
| DER 332 | 126.6 ± 30.1$^b$ | 3524.6 ± 124.6$^b$ | 6.3 ± 0.9$^b$ | 7.7 ± 1.2 | 168 |
| ESO | \ | \ | \ | \ | 37 |

$^a$at yielding point.
$^b$at breaking point. From K. Huang, P. Zhang, J. Zhang, S. Li, M. Li, J. Xia, Y. Zhou, Green Chemistry 2013, 15, 2466-2475

Referring to FIG. 1, the monomer production process 100 charges a sodium hydroxide solution in an ethanol-H$_2$O mixture into a container (block 102). The sodium hydroxide may be 16 g solution. The ethanol-H$_2$O may be a 140 mL solution (1:1, V/V). The container may be a 1-L three-necked round-bottom flask equipped with reflux condenser, magnetic stirrer, and thermometer. The solution is heated to 70° C. (block 104). Hempseed oil is added dropwise added to the solution (block 106). 100 g of hempseed oil may be added utilizing a dropping funnel. The reaction is continued at 70° C. for 2 hours (block 108). The reaction mixture is adjusted to pH 2-3 (block 110). 1 M hydrochloric acid may be utilize to adjust the pH. The reaction is continued at 70° C. for another hour (block 112). The mixture is cooled (block 114). The mixture is extracted (block 116). Ethyl ether may be utilized as well as de-ionized (DI) water (e.g., washed three times). The solution is dried (block 118). The ethyl ether solution may be dried over magnesium sulfate. Vacuum distillation is performed to remove the ethyl ether (block 120). The result is a viscous liquid hydrolyzed hempseed oil. The content of fatty acids in hydrolylzed hempseed oil may be estimated using Gas Chromatography-Flame Ionization Detector (GC-FID) by a standard fatty acid methyl esters (FAME) procedure. The HFA is directly acrylated in the presence of BF$_3$.Et$_2$O at 80° C. for 4 hours (block 122). The reaction conditions may be the mixture of HFA, acrylic acid (AA) and BF$_3$.Et$_2$O in a molar ratios of 1:27.4:1.37 under stirring. Depending on the size of reaction, two different procedures may be employed. For the small size reactions, the excess AA and catalyst are removed by NaHCO$_3$ aq. washing directly. For the large size reactions, the excess AA and catalyst are recovered by distillation at 35-45° C. under reduced pressure, and the recovered AA and catalyst are reused. The yellow liquid acrylated hempseed fatty acid (AHFA) is obtained. The AHFA, benzyltrimethylammonium bromide (BTMAB), and hydroquinone is charged (block 124). A 100-mL round-bottom flask equipped with a magnetic stirrer may be utilized into which to charge 0.10 mol AHFA, 0.002 mol (2 mol % on fatty acid) of BTMAB, and 1 wt % hydroquinone. The mixture is warmed under argon atmosphere for about 15 minutes in an oil bath preheated to 120° C. (block 126). Glycidyl methacrylate (GMA) is then added dropwise (block 128). 0.11 mol of GMA maybe be added utilizing a dropping funnel. The reaction progress may be monitored over 6 hours by thin layer chromatograph (TLC) using methylene chloride and ethyl acetate (7:3). Due to the competing side reactions, further addition of up to 0.1 molar equivalent of GMA and additional reaction time may be utilized to react all of the AHFA. The reaction mixture is reacted for 8-10 hours (130 130). Two major oxirane ring-opening products may be produced.

In some embodiments, a purified sample is produced. The dark-colored reaction mixture may be cooled to room temperature and then passed through a short silica (200 mesh) column using 20% ethyl acetate in methylene chloride to remove the catalyst and dark brown particulates. A yellowish brown liquid is obtained.

Figure 2:
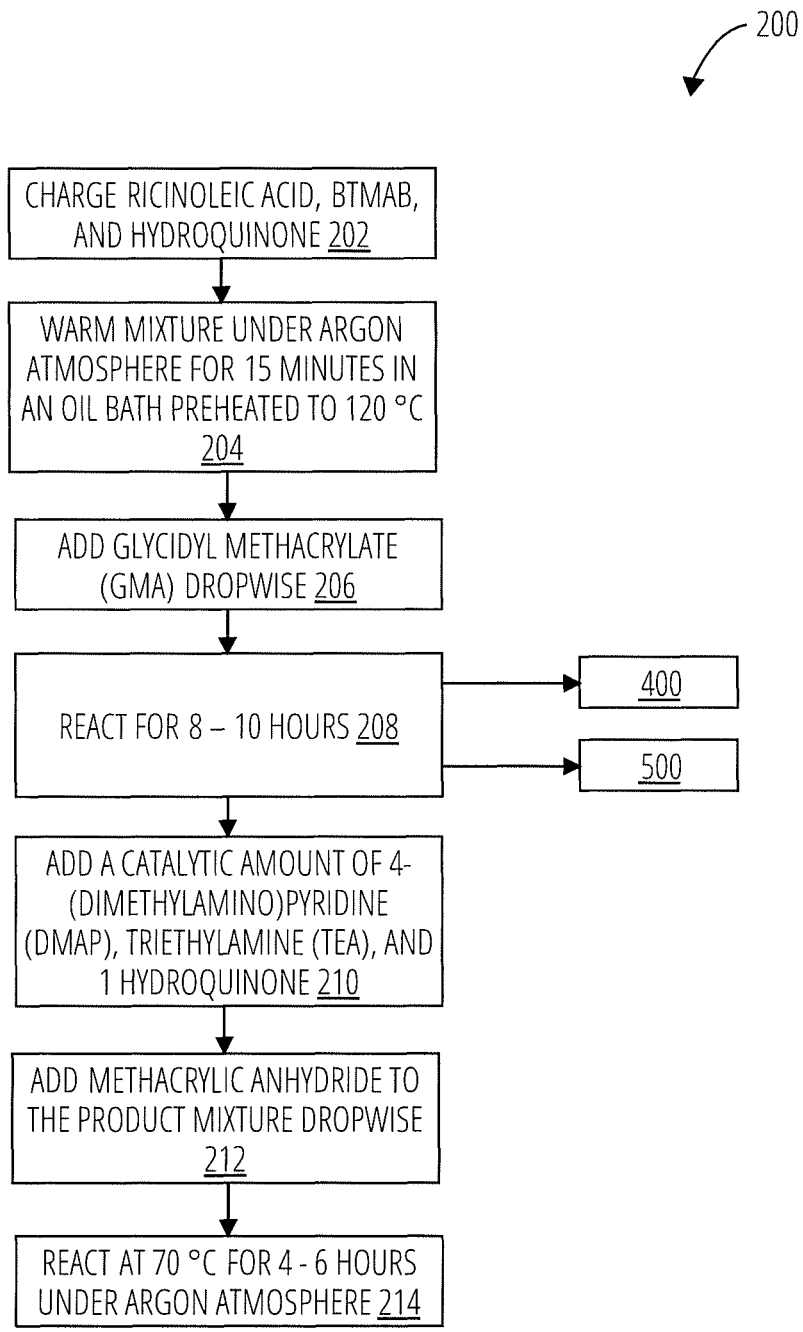
FIG. 2 illustrates an embodiment of a monomer production process 200.

Referring to FIG. 2, the monomer production process 200 charges ricinoleic acid, BTMAB, and hydroquinone (block 202). The ricinoleic acid, BTMAB, and hydroquinone may be charged into a 100-mL round-bottom flask equipped with a magnetic stirrer. 29.85 g (0.10 mol) ricinoleic acid (RA), 0.46 g (0.002 mol, 2 mol % on the basis of fatty acid) BTMAB, and 0.3 g (1 wt %) of hydroquinone may be utilized. The mixture is warmed under argon atmosphere for 15 minutes in an oil bath preheated to 120° C. (block 204). Glycidyl methacrylate (GMA) is added dropwise (block 206). 15.63 g (1.1 equivalent) of GMA may be added utilizing a dropping funnel. The reaction progress may be monitored over 6 hours by TLC. Due to the competing side reactions, further addition of up to 0.1 equivalent of GMA and additional reaction time may be utilized to ensure all of the RA reacted. The reaction proceeds for 8-10 hours (block 208). Two major oxirane ring-opening products are produced. To prepare the purified sample for characterizations, the dark-colored reaction mixture may be cooled to room temperature and passed through a short silica (200 mesh) column using 20% ethyl acetate in methylene chloride to remove the catalyst and dark brown particulates. A yellowish brown liquid (RA-GMA) is obtained. A catalytic amount of 4-(dimethylamino)pyridine (DMAP), triethylamine (TEA) (3 molar excess), and hydroquinone are added (block 210). 0.12 g, 1 mol % of 4-(dimethylamino)pyridine (DMAP), 30.35 g triethylamine (TEA) (3 molar excess), and 1 wt % hydroquinone may be added. Methacrylic anhydride is added to the product mixture dropwise (block 212). 46.25 g, 0.3 mol; 3 equivalent to RA of methacrylic anhydride may be added to the product mixture. The reaction proceeds at 70° C. for 4-6 hours under argon atmosphere (block 214). The reaction may be monitored by TLC, which determined the presence of one major product in addition to some minor impurities that account for unreacted excess methacrylic anhydride, residual traces of GMA and dimethacrylates.

In some embodiments, the resultant is purified. The reddish brown reaction mixture is dissolved in ~300 mL of methylene chloride and washed with 500 mL (6×~80 mL) each of distilled H$_2$O, 10% (v/v) dilute hydrochloric acid, saturated sodium bicarbonate (NaHCO$_3$) solution and saturated brine. The organic phase is dried over anhydrous magnesium sulfate (MgSO$_4$) and concentrated under reduced pressure at no more than 60° C., yielding ~40 g yellowish-dark brown liquid product (MARA-GMA). To prevent premature gelation, the product is stored in a closed container, away from direct sunlight, UV, and heat sources.

Figure 3:
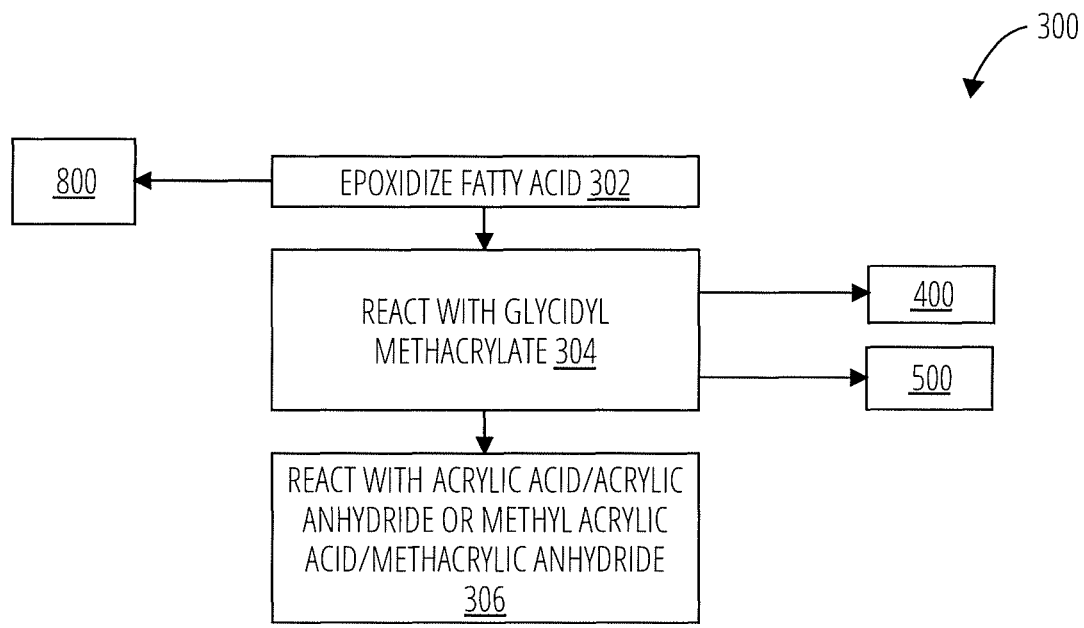
FIG. 3 illustrates an embodiment of a monomer production process 300.

Referring to FIG. 3, the monomer production process 300 epoxidizes the fatty acid. The fatty acid may be epoxidized by mixing 28 g of HFA and 21.2 g of sodium carbonate in 20 mL methylene chloride ($CH_2Cl_2$). 73.6 g meta-chloroperoxybenzoic acid (m-CPBA, 75 wt %) dissolved in $CH_2Cl_2$ at 0.1 g/ml concentration may then be added dropwise at a reaction temperature below 15° C., and then the reaction is reacted for 4 hours to complete the epoxidation. The reaction mixture may be washed with 10 wt % sodium sulfite and then by 10 wt % aqueous sodium bicarbonate. $CH_2Cl_2$ is removed by in vacuum rotary evaporation and 30 g product epoxidized hempseed oil fatty acid (EHFA, 96% yield) is obtained. The product is then reacted with glycidyl methacrylate (block 304). First, 31.2 g EHFA, 0.46 g, BTMAB and 0.3 g (1 wt %) of hydroquinone may be mixed in a flask. The mixture may be protected under argon atmosphere and placed in an oil bath of 120° C. for about 15 minutes. Glycidyl methacrylate (GMA, 15.63 g (1.1 equivalent)) is then added dropwise. The reaction progress is monitored over 6 hours by TLC. The reaction mixture may then be purified by silica gel column to remove the impurity by ethyl acetate and methylene chloride, then product EHFA-GMA is obtained. EHFA-GMA is reacted with either acrylic acid/ acrylic anhydride or methacrylic acid methacrylic anhydride (block 306). 45.4 g EHFA-GMA, 1.15 g BTMAB, and 0.9 g (2 wt %) of hydroquinone is mixed and allowed to warm under argon atmosphere for about 15 minutes in an oil bath preheated to 100° C. The mixture of acrylic acid/acrylic anhydride (R=H) or methyl acrylic acid/methacrylic anhydride (R=$CH_3$) (acid/anhydride=0.15 mol/0.3 mol) is added dropwise into the reaction mixture. The reaction progress is monitored over 6 hours by TLC. Subsequently, the reaction mixture is purified by silica gel column to remove the impurity by ethyl acetate and methylene chloride.

Figure 4:
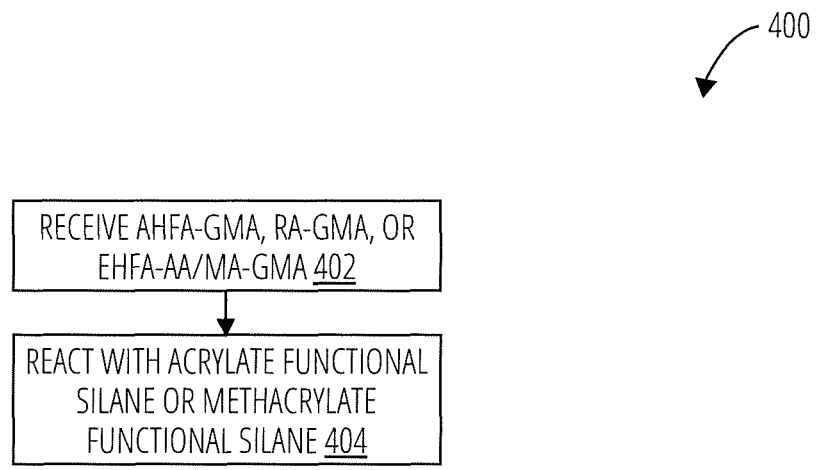
FIG. 4 illustrates an embodiment of a monomer production process 400.

Referring to FIG. 4, the monomer production process 400 receives AHFA-GMA, RA-GMA, or EHFA-AA/MA-GMA (block 402). The received compound is reacted with an acrylate silane group (block 404). The reactions may be carried out in a flask equipped with a stirrer, dropping funnel, thermometer, and reflux condenser capped with a drying tube. The silane agent may be mixed with AHFA-GMA, RA-GMA, or EHFA-AA/MA-GMA at a molar ratio of 1:1 to 1:4 (based on the hydroxyl groups containing in the reagents), and the mixture may be stirred for 2-3 h at 90-100° C. Liberated methanol may be distilled off under reduced pressure (on a rotary evaporator), giving the products of AHFA-GMA-A-Silane, RA-GMA-A-Silane, or EHFA-AA/MA-GMA-A-Silane. A methacrylate functional group may also be utilized to produce AHFA-GMA-MA-Silane, RA-GMA-MA-Silane, or EHFA-AA/MA-GMA-MA-Silane when using methacrylate silane as the silane agent.

Figure 5:
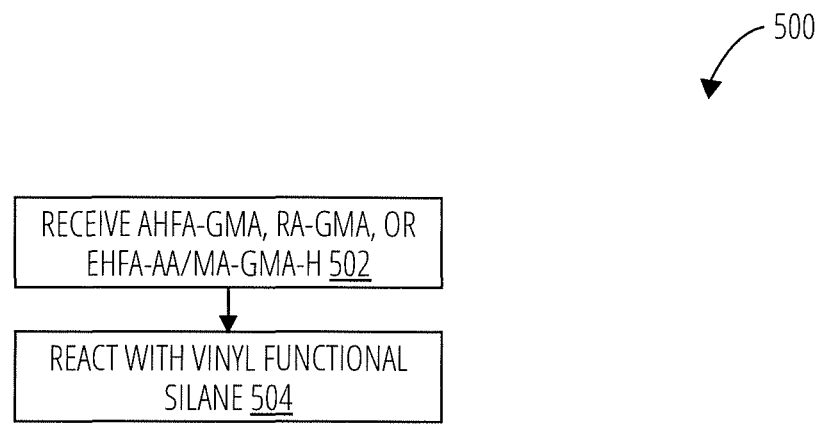
FIG. 5 illustrates an embodiment of a monomer production process 500.

Referring to FIG. 5, the monomer production process 500 receives AHFA-GMA, RA-GMA, or EHFA-AA/MA-GMA (block 502). The compounds are reacted with vinyl functional silane (block 504). The reactions may be carried out in a flask equipped with a stirrer, dropping funnel, thermometer, and reflux condenser capped with a drying tube. The silane agent may be mixed with AHFA-GMA, RA-GMA or EFA-AA/MA-GMA-H at a molar ratio of 1:1 to 1:4 (based on the hydroxyl groups containing in the reagents), and the mixture may be stirred for 2-3 h at 90-100° C. Liberated methanol may be distilled off under reduced pressure (on a rotary evaporator), to produce AHFA-GMA-V-Silane, RA-GMA-V-Silane, and EHFA-AA/MA-H—V-Silane.

Figure 6:
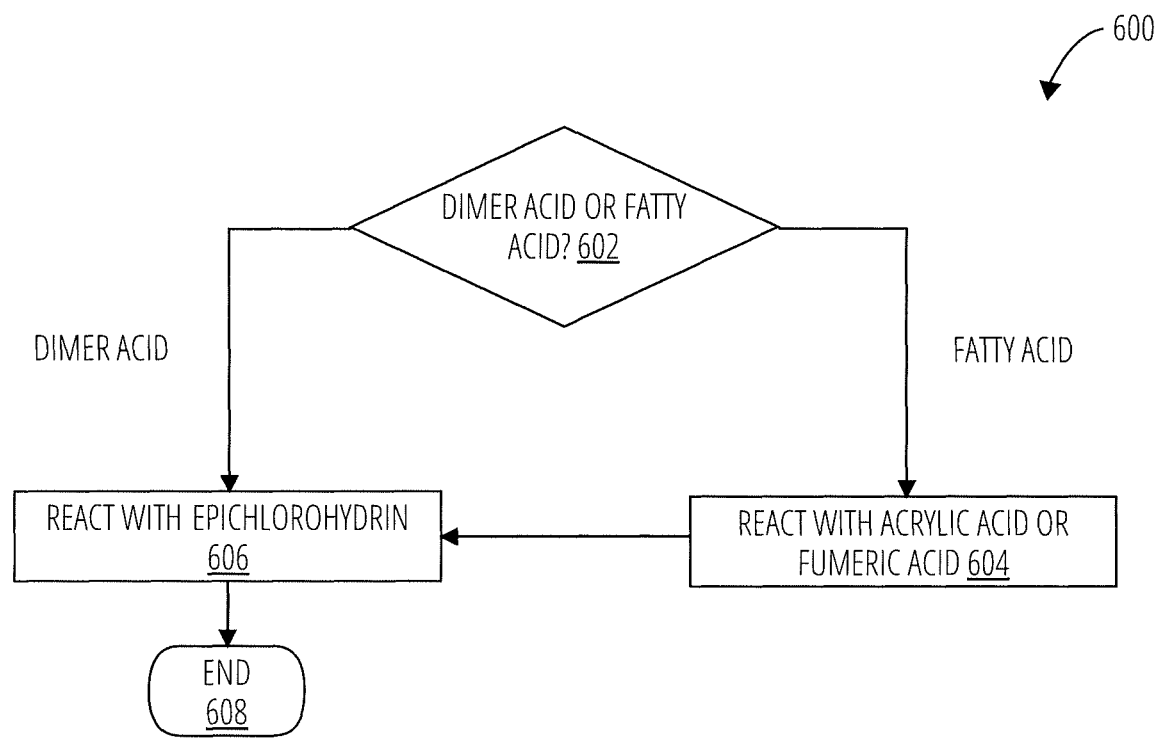
FIG. 6 illustrates an embodiment of a monomer production process 600.

Referring to FIG. 6, the monomer production process 600 determines whether a dimer acid or a fatty acid is received (decision block 602). If a fatty acid is received, the fatty acid is reacted with either acrylic acid or fumaric acid to produce a fatty acid-derived diacid or fatty acid-derived triacid (block 604). To produce FA-triacid, 129 g of crude adduct of fumaric acid and conjugated FA may be dissolved in 500 mL acetone and neutralized by 50% NaOH solution drop by drop until the pH value reaches 7. After the acetone is removed, the precipitated tricarboxylic acid may then be extracted with ethyl acetate. The organic layer may be neutralized using HCl and dried by $NaSO_4$ for 12 h and then the ethyl acetate may be removed using a vacuum rotary evaporator to obtain a white solid FA-triacid. To produce FA-diacid, fatty acids (100 g) and hydroquinone (0.25 g) are charged into a flask. The temperature is raised to 160° C., and acrylic acid (24.7 g) may be added slowly. The reaction is continued for 5 h at 160° C. after all the acrylic acid is added. The excess acrylic acid is first removed using a rotary evaporator under vacuum, and then the crude product may be distilled under a 5 mmHg vacuum. The fraction between 210 to 240° C. is collected, the yellowish liquid FA-diacid.

The dimer acid, fatty acid-derived diacid, or fatty acid-derived triacid are then reacted with epichlorohydrin to produce an epoxy (block 606). If a dimer acid, a 50 mL flask equipped with reflux condenser, magnetic stirrer, and thermometer may be charged with 3.74 g DA, 18.5 g epichlorohydrin, and 0.023 g benzyltriethyl ammonium chloride. The reaction temperature may then be raised to 117° C. and the reaction continued at that temperature for 2 h. The mixture may be cooled to 60° C., 0.8 g sodium hydroxide and 1.12 g calcium oxide is charged. The mixture may then be stirred at 60° C. for 3 h and then filtered by diatomaceous earth (e.g., Celite®) and filter paper. The solid is discarded. After the excess epichlorohydrin is distilled under vacuum at 100° C. from the filtrate, a light yellowish liquid product of DA-diepoxy is obtained. If a FA-triacid, 3.5 g FA-triacid, 18.5 g epichlorohydrin and 0.061 g benzyltriethyl ammonium chloride are added to a 50-mL flask are added. The reaction temperature is raised to 117° C. and the reaction continued for 2 h. After the mixture is cooled to 60° C., 1.2 g sodium hydroxide and 1.68 g calcium oxide are charged. The mixture is stirred at 60° C. for 3 h and then filtered with powder Celite. After the excess epichlorohydrin is distilled under vacuum at 100° C. from the filtrate, a yellowish viscous product (4.56 g) is obtained. The product is purified using a silica gel column (ethyl acetate:hexane=1:4 v/v) to receive 4.00 g of FA-triepoxy with an epoxide equivalent weight 193 g/mol (theory: 187 g/mol). The synthesis of FA-diepoxy may be similar to that of FA-triepoxy. The product may be purified using a silica gel column (ethyl acetate:hexane=1:4 v/v), and the yield of pure FA-diepoxy may be 85%. The EEW of FA-diepoxy is 235 g/mol (theory: 231 g/mol). The monomer production process 600 then ends (done block 608).

Figure 7:
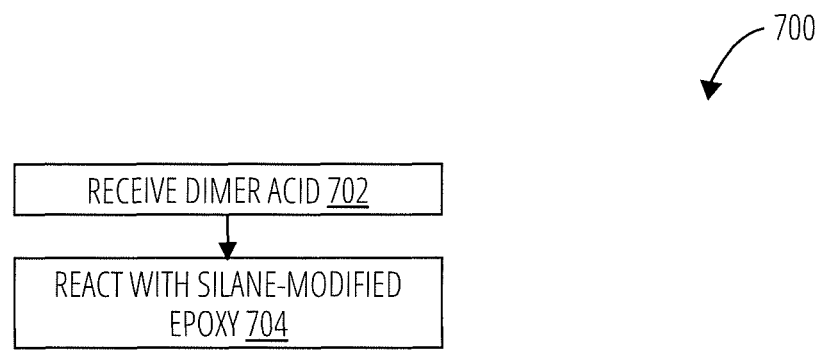
FIG. 7 illustrates an embodiment of a monomer production process 700.

Referring to FIG. 7, the monomer production process 700 receives a dimer acid (block 702). The dimer acid is then reacted with a silane-modified epoxy (block 704). Silicon epoxy compound 59 g, DA 50 g, toluene 75 g, and trifluoroacetic acid 0.37 g may be charged into a 250 mL flask equipped with a nitrogen gas, thermometer and Dimroth condenser. The reaction may first be conducted at 120° C. under stirring for 1 hour; subsequently, the temperature may be gradually raised to 140° C. by distillation removing the generated methanol with toluene. The reaction is continued for 3 hours at 140° C., and then the remaining toluene is distilled off under reduced pressure. A transparent liquid product of DA-diepoxy-Silane is produced.

Figure 8:
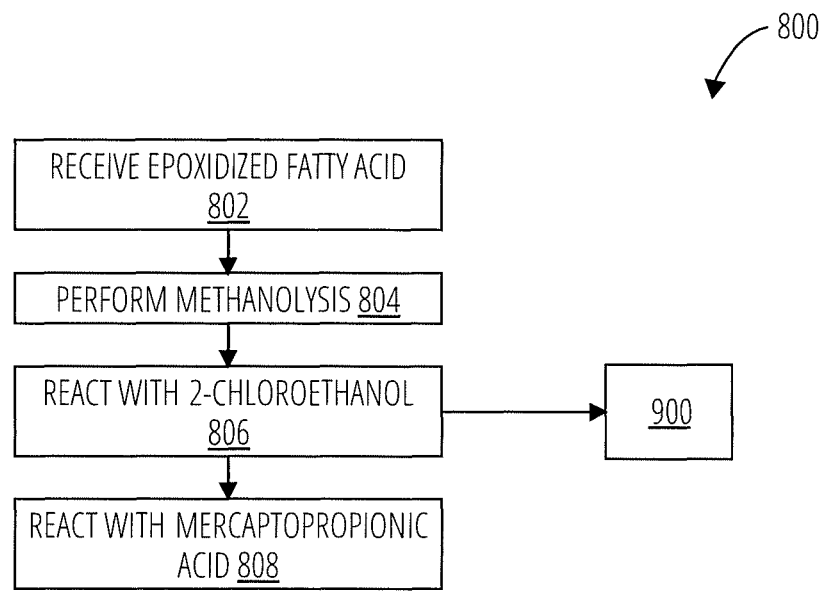
FIG. 8 illustrates an embodiment of a monomer production process 800.

Referring to FIG. 8, the monomer production process 800 receives an epoxidized fatty acid (block 802). The epoxidized fatty acid then undergoes methanolysis to produce MEHFA (block 804). MEHFA may be synthesized by oxirane ring opening reaction via refluxing EHFA (100 g) with excess methanol (136 g) in the presence of tetra-fluoroboric acid catalyst. The molar ratio of epoxy groups to methanol may be 1:11. The concentration of the catalyst may be 1% of the total weight of the EHFA and methanol. HFA, methanol and catalyst (amount of each reagent as described above) are added into a flask, then stirred and reflux for 1 h. After cooled to room temperature, ammonia (30% in water) is added to neutralize the reaction mixture pH to 7. The solvent is removed on a rotary evaporator under a low vacuum at 60-95° C. The MEHFA is then reacted with 2-chloroethanol (block 806). Hydroquinone (3.0 g) and NaOH (8 g) may be added to the mixture of 75.2 g MEHFA and 48.3 g 2-chloroethanol at room temperature and under stirring. After the mixture is refluxed for 4 h, it may be cooled down to room temperature and filtered to remove the precipitate. The filtrate is added to a large amount of water, and the product MEHFA-triol is precipitated. The MEHFA-triol is reacted with mercaptopropionic acid to produce the FA-derived thio compound (block 808). The mixture of MEHFA-triol (42.0 g), 3-Mercaptopropionic acid (40.0 g), and 1 wt % p-toluenesulfonic acid (p-TSA) solution (200 mL) in toluene in a 500 mL flask may be refluxed for 4 h. After cooled down, the mixture may be extracted by ethyl estate and the organic layer is washed by water. After the solvent is removed by rotatory evaporator, the resulting solid is dried by MgSO4 to give the product.

Figure 9:
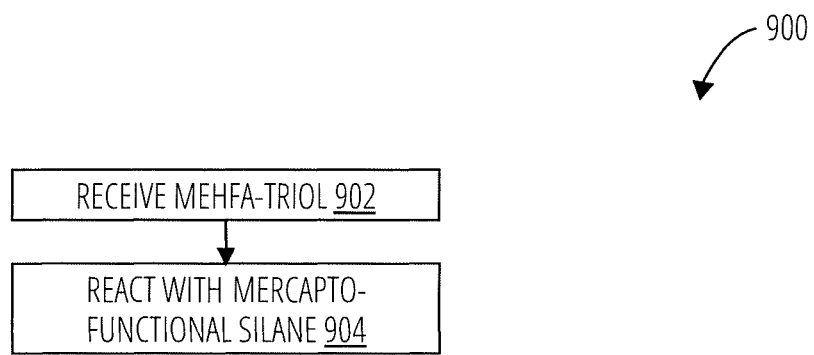
FIG. 9 illustrates an embodiment of a monomer production process 900.

Referring to FIG. 9, the monomer production process 900 receives MEHFA-triol (block 902). The MEHFA-triol is reacted with mercapto-functional silane (block 904). The reaction procedure may be similar to that depicted in the monomer production process 400. MEHFA-triol-silane is obtained.

What is claimed is:

1. A compound having a structure of Formula II:

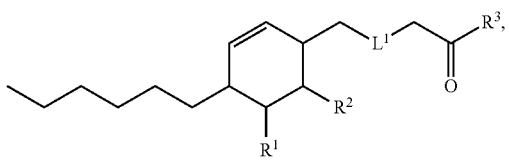

wherein:

$R^1$ and $R^2$ are each independently hydrogen,

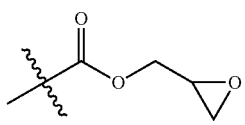 [SMILES: *C(=O)OCC1CO1]

or

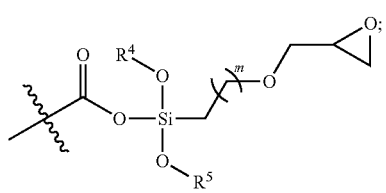

$R^3$ is 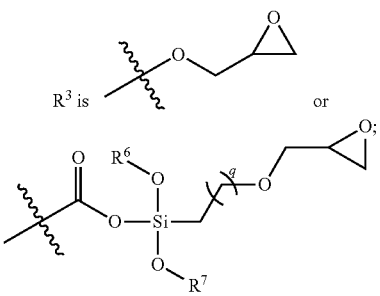

$R^4$ and $R^5$ are, at each occurrence, independently methyl or ethyl;

$R^6$ and $R^7$ are each independently methyl or ethyl;

m is an integer ranging from 0 to 5;

q is an integer ranging from 0 to 5; and $L^1$ is a $C_1$-$C_9$alkylene or a $C_1$-$C_9$alkenylene.

2. The compound of claim 1, wherein $R^1$ has the following structure:

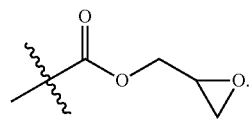 [SMILES: *C(=O)OCC1CO1]

3. The compound of claim 1, wherein $R^2$ has the following structure:

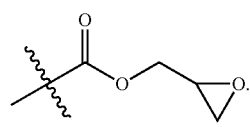 [SMILES: *C(=O)OCC1CO1]

4. The compound claim 1, wherein $R^3$ has the following structure:

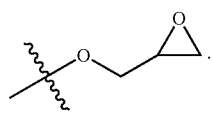 [SMILES: *OCC1CO1]

5. The compound of claim 1, wherein $L^1$ is a $C_1$-$C_9$ alkylene.

6. The compound of claim 5, wherein $L^1$ is a $C_5$ alkylene.

7. The compound of claim 1, wherein $R^1$ has the following structure:

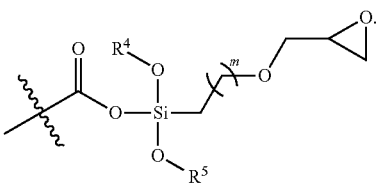

8. The compound of claim 7, wherein $R^4$ and $R^5$ are both methyl, and m is 2.

9. The compound of claim 1, wherein $R^1$ is hydrogen.

10. The compound claim 1, wherein $R^2$ has the following structure:
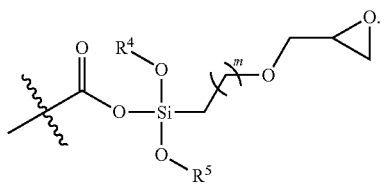
11. The compound of claim 10, wherein $R^4$ and $R^5$ are both methyl, and m is 2.
12. The compound of claim 11, wherein $R^3$ has the following structure:
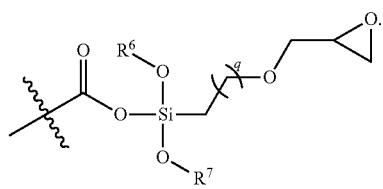
13. The compound of claim 12, wherein $R^6$ and $R^7$ are both methyl, and q is 2.
14. The compound of claim 11, wherein the compound of Formula II has one of the following structures:
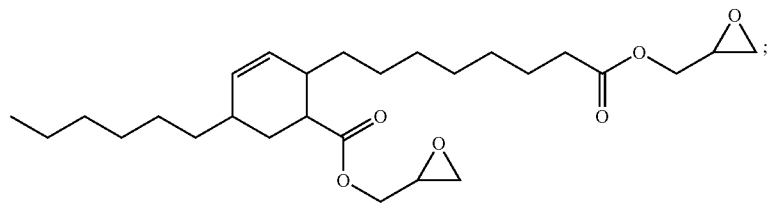
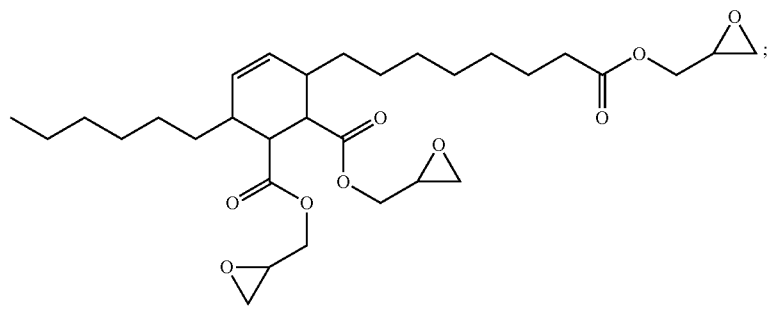
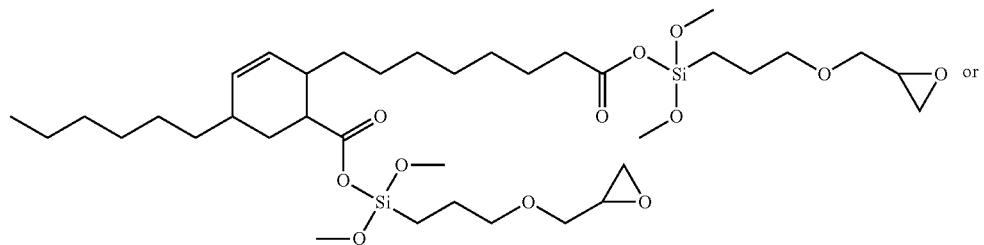
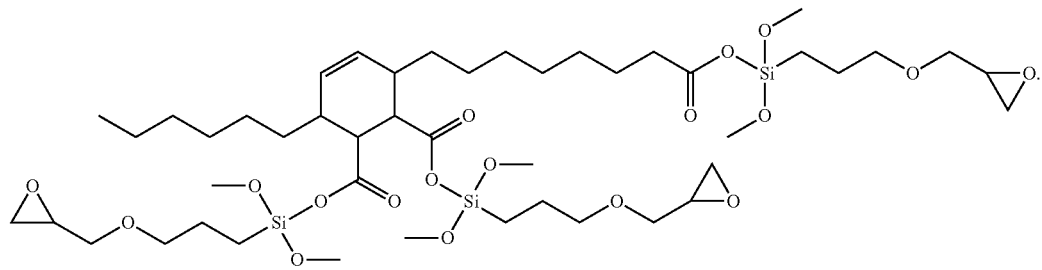

15. A composition comprising the compound of claim 1 and a second compound.

16. The composition of claim 15, wherein $R^1$ has the following structure:

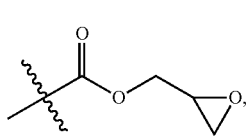 [SMILES: *C(=O)OCC1CO1]

$R^2$ has the following structure:

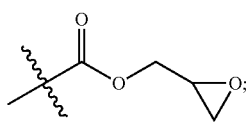 [SMILES: *C(=O)OCC1CO1]

and
$R^3$ has the following structure:

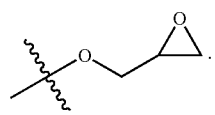 [SMILES: *OCC1CO1]

17. The composition of claim 15, wherein $R^1$ is hydrogen.

18. The composition of claim 15, wherein $R^2$ has the following structure:

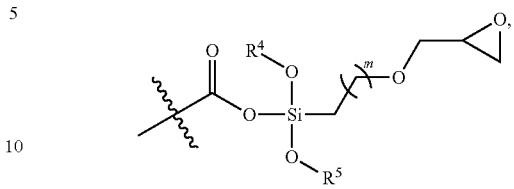

wherein:
$R^3$ has the following structure:

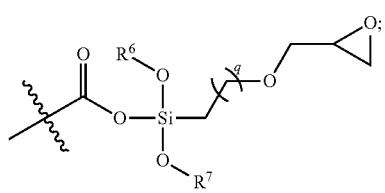

$R^4$ and $R^5$ are both methyl; and
m is 2.

19. The composition of claim 18, wherein the compound has one of the following structures:

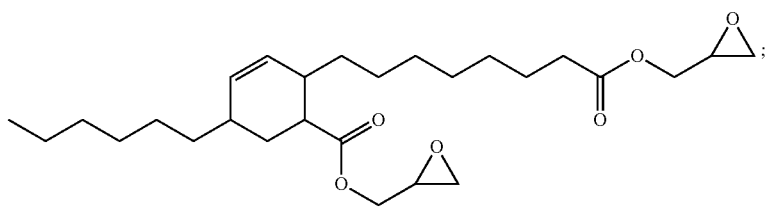

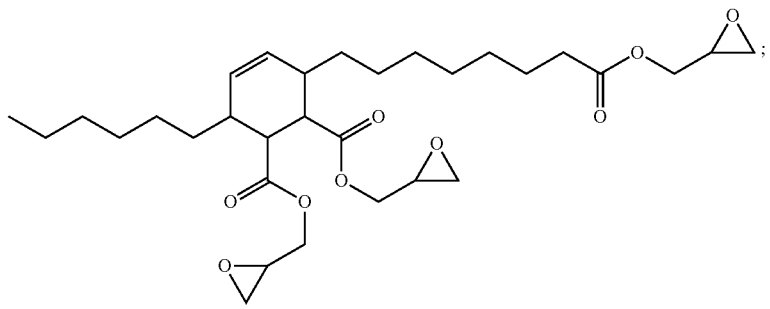

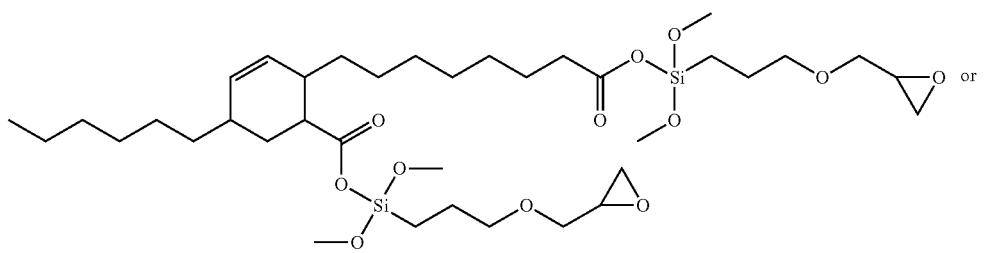

-continued
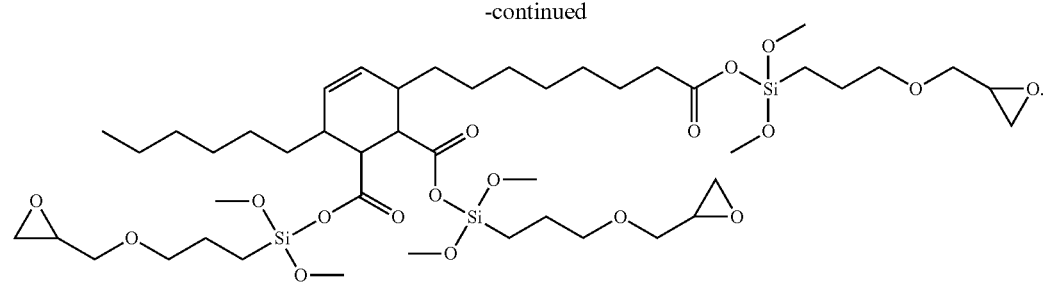
* * * * *